(12) United States Patent
Woloszko et al.

(10) Patent No.: US 7,297,143 B2
(45) Date of Patent: Nov. 20, 2007

(54) TEMPERATURE INDICATING ELECTROSURGICAL APPARATUS AND METHODS

(75) Inventors: Jean Woloszko, Austin, TX (US); Robert H. Dahla, Sunnyvale, CA (US); Michael A. Baker, Austin, TX (US); James L. Pacek, Lakeway, TX (US)

(73) Assignee: ArthroCare Corporation, Austin, TX (US)

( * ) Notice: Subject to any disclaimer, the term of this patent is extended or adjusted under 35 U.S.C. 154(b) by 44 days.

(21) Appl. No.: 10/774,222

(22) Filed: Feb. 5, 2004

(65) Prior Publication Data

US 2004/0186469 A1    Sep. 23, 2004

Related U.S. Application Data

(60) Provisional application No. 60/445,405, filed on Feb. 5, 2003.

(51) Int. Cl.
*A61B 18/18* (2006.01)
*A61B 5/00* (2006.01)

(52) U.S. Cl. .................... 606/41; 607/102

(58) Field of Classification Search .......... 606/31, 606/41, 42, 45–50; 607/101, 102; 600/549
See application file for complete search history.

(56) References Cited

U.S. PATENT DOCUMENTS

| 2,056,377 | A | 10/1939 | Wappler |
|---|---|---|---|
| 3,633,425 | A | 1/1972 | Sanford |
| 3,707,149 | A | 12/1972 | Hao et al. |
| 3,815,604 | A | 6/1974 | O'Malley et al. |
| 3,828,780 | A | 8/1974 | Morrison, Jr. et al. |
| 3,901,242 | A | 8/1975 | Storz |
| 3,920,021 | A | 11/1975 | Hiltebrandt |
| 3,939,839 | A | 2/1976 | Curtiss |
| 3,970,088 | A | 7/1976 | Morrison |
| 4,040,426 | A | 8/1977 | Morrison, Jr. |
| 4,043,342 | A | 8/1977 | Morrison, Jr. |
| 4,074,718 | A | 2/1978 | Morrison, Jr. |
| 4,092,986 | A | 6/1978 | Schneiderman |
| 4,116,198 | A | 9/1978 | Roos |
| 4,181,131 | A | 1/1980 | Ogiu |
| 4,184,492 | A | 1/1980 | Meinke et al. |
| 4,202,337 | A | 5/1980 | Hren et al. |

(Continued)

FOREIGN PATENT DOCUMENTS

DE    3930451 A1    3/1991

(Continued)

OTHER PUBLICATIONS

PCT International Search Report for PCT/US04/03614, 1 page.

(Continued)

*Primary Examiner*—Michael Peffley
(74) *Attorney, Agent, or Firm*—Brian E. Szymczak

(57) ABSTRACT

Systems, apparatus, and methods for monitoring temperature at a region near a surgical site during a procedure. A temperature-indicating element of an electrosurgical device comprises an indicator composition adapted to undergo a change in appearance in response to a pre-defined temperature range. The change in appearance of the temperature-indicating element indicates to the operator of the device a temperature condition at the working end of the device.

42 Claims, 13 Drawing Sheets

U.S. PATENT DOCUMENTS

| | | | |
|---|---|---|---|
| 4,228,800 A | 10/1980 | Degler, Jr. et al. | |
| 4,232,676 A | 11/1980 | Herczog | |
| 4,248,231 A | 2/1981 | Herczog et al. | |
| 4,326,529 A | 4/1982 | Doss et al. | |
| 4,381,007 A | 4/1983 | Doss | |
| 4,418,692 A | 12/1983 | Guay | 606/42 |
| 4,474,179 A | 10/1984 | Koch | 606/40 |
| 4,476,862 A | 10/1984 | Pao | |
| 4,532,924 A | 8/1985 | Auth et al. | |
| 4,548,207 A | 10/1985 | Reimels | |
| 4,567,890 A | 2/1986 | Ohta et al. | |
| 4,580,557 A | 4/1986 | Hertzmann | |
| 4,587,975 A | 5/1986 | Salo et al. | |
| 4,590,934 A | 5/1986 | Malis et al. | |
| 4,593,691 A | 6/1986 | Lindstrom et al. | |
| 4,658,817 A | 4/1987 | Hardy | |
| 4,660,571 A | 4/1987 | Hess et al. | |
| 4,674,499 A | 6/1987 | Pao | |
| 4,682,596 A | 7/1987 | Bales et al. | |
| 4,706,667 A | 11/1987 | Roos | |
| 4,709,698 A | 12/1987 | Johnston et al. | |
| 4,727,874 A | 3/1988 | Bowers et al. | |
| 4,765,331 A | 8/1988 | Petruzzi et al. | |
| 4,785,823 A | 11/1988 | Eggers et al. | |
| 4,805,616 A | 2/1989 | Pao | |
| 4,823,791 A | 4/1989 | D'Amelio et al. | |
| 4,832,048 A | 5/1989 | Cohen | |
| 4,860,752 A | 8/1989 | Turner | |
| 4,907,589 A | 3/1990 | Cosman | 606/34 |
| 4,920,978 A | 5/1990 | Colvin | |
| 4,931,047 A | 6/1990 | Broadwin et al. | |
| 4,936,281 A | 6/1990 | Stasz | |
| 4,936,301 A | 6/1990 | Rexroth et al. | |
| 4,943,290 A | 7/1990 | Rexroth et al. | |
| 4,955,377 A | 9/1990 | Lennox et al. | |
| 4,966,597 A | 10/1990 | Cosman | |
| 4,967,765 A | 11/1990 | Turner et al. | |
| 4,976,711 A | 12/1990 | Parins et al. | |
| 4,979,948 A | 12/1990 | Geddes et al. | |
| 4,998,933 A | 3/1991 | Eggers et al. | |
| 5,007,908 A | 4/1991 | Rydell | |
| 5,009,656 A | 4/1991 | Reimels | |
| 5,035,696 A | 7/1991 | Rydell | |
| 5,047,026 A | 9/1991 | Rydell | |
| 5,047,027 A | 9/1991 | Rydell | |
| 5,057,105 A | 10/1991 | Malone et al. | |
| 5,057,106 A | 10/1991 | Kasevich et al. | |
| 5,057,743 A | 10/1991 | Krasko et al. | |
| 5,078,717 A | 1/1992 | Parins et al. | |
| 5,080,660 A | 1/1992 | Buelna | |
| 5,083,565 A | 1/1992 | Parins et al. | |
| 5,084,044 A | 1/1992 | Quint | |
| 5,085,659 A | 2/1992 | Rydell | |
| 5,088,997 A | 2/1992 | Delahuerga et al. | |
| 5,092,339 A | 3/1992 | Geddes et al. | |
| 5,098,431 A | 3/1992 | Rydell | |
| 5,099,840 A | 3/1992 | Goble et al. | |
| 5,102,410 A | 4/1992 | Dressel | |
| 5,108,391 A | 4/1992 | Flachenecker et al. | |
| RE33,925 E | 5/1992 | Bales et al. | 606/48 |
| 5,112,330 A | 5/1992 | Nishigaki et al. | |
| 5,122,138 A | 6/1992 | Manwaring | |
| 5,125,928 A | 6/1992 | Parins et al. | |
| 5,156,151 A | 10/1992 | Imran | |
| 5,167,659 A | 12/1992 | Ohtomo et al. | |
| 5,171,311 A | 12/1992 | Rydell et al. | |
| 5,178,620 A | 1/1993 | Eggers et al. | |
| 5,183,338 A | 2/1993 | Wickersheim et al. | |
| 5,190,517 A | 3/1993 | Zieve et al. | |
| 5,192,280 A | 3/1993 | Parins | |
| 5,195,959 A | 3/1993 | Smith | |
| 5,197,466 A | 3/1993 | Marchosky et al. | |
| 5,197,963 A | 3/1993 | Parins | |
| 5,207,675 A | 5/1993 | Canady | |
| 5,217,457 A | 6/1993 | Delahuerga et al. | |
| 5,217,459 A | 6/1993 | Kamerling | |
| 5,249,585 A | 10/1993 | Turner et al. | |
| 5,255,980 A | 10/1993 | Thomas et al. | |
| 5,261,410 A | 11/1993 | Alfano et al. | |
| 5,267,994 A | 12/1993 | Gentelia et al. | |
| 5,267,997 A | 12/1993 | Farin et al. | |
| 5,273,524 A | 12/1993 | Fox et al. | |
| 5,277,201 A | 1/1994 | Stern | |
| 5,281,216 A | 1/1994 | Klicek | |
| 5,281,218 A | 1/1994 | Imran | |
| 5,290,282 A | 3/1994 | Casscells | |
| 5,300,069 A | 4/1994 | Hunsberger et al. | |
| 5,306,238 A | 4/1994 | Fleenor | |
| 5,312,400 A | 5/1994 | Bales et al. | |
| 5,314,406 A | 5/1994 | Arias et al. | |
| 5,318,563 A | 6/1994 | Malis et al. | |
| 5,324,254 A | 6/1994 | Phillips | |
| 5,330,470 A | 7/1994 | Hagen | |
| 5,334,140 A | 8/1994 | Phillips | |
| 5,334,183 A | 8/1994 | Wuchinich | |
| 5,334,193 A | 8/1994 | Nardella | |
| 5,336,220 A | 8/1994 | Ryan et al. | |
| 5,336,443 A | 8/1994 | Odashima | |
| 5,342,357 A | 8/1994 | Nardella | |
| 5,348,554 A | 9/1994 | Imran et al. | |
| 5,366,443 A | 11/1994 | Eggers et al. | |
| 5,370,675 A | 12/1994 | Edwards et al. | |
| 5,374,261 A | 12/1994 | Yoon | |
| 5,375,588 A | 12/1994 | Yoon | |
| 5,380,277 A | 1/1995 | Phillips | |
| 5,380,316 A | 1/1995 | Aita | |
| 5,383,876 A | 1/1995 | Nardella | |
| 5,383,917 A | 1/1995 | Desai et al. | |
| 5,389,096 A | 2/1995 | Aita | |
| 5,395,312 A | 3/1995 | Desai | |
| 5,400,267 A | 3/1995 | Denen et al. | |
| 5,401,272 A | 3/1995 | Perkins | |
| 5,403,311 A | 4/1995 | Abele et al. | |
| 5,417,687 A | 5/1995 | Nardella et al. | |
| 5,419,767 A | 5/1995 | Eggers et al. | |
| 5,423,810 A | 6/1995 | Goble et al. | |
| 5,423,882 A | 6/1995 | Jackman et al. | |
| 5,436,566 A | 7/1995 | Thompson et al. | |
| 5,437,662 A | 8/1995 | Nardella | |
| 5,438,302 A | 8/1995 | Goble | |
| 5,441,499 A | 8/1995 | Fritzsch | |
| 5,451,224 A | 9/1995 | Goble et al. | |
| 5,454,809 A | 10/1995 | Janssen | |
| 5,458,596 A | 10/1995 | Lax et al. | |
| 5,458,597 A | 10/1995 | Edwards et al. | |
| 5,472,443 A | 12/1995 | Cordis et al. | |
| 5,496,312 A | 3/1996 | Klicek | |
| 5,496,314 A | 3/1996 | Eggers | |
| 5,496,317 A | 3/1996 | Goble et al. | |
| 5,505,730 A | 4/1996 | Edwards et al. | |
| 5,514,130 A | 5/1996 | Baker | |
| 5,542,915 A | 8/1996 | Edwards et al. | |
| 5,554,152 A | 9/1996 | Aita | |
| 5,556,397 A | 9/1996 | Long et al. | |
| 5,562,703 A | 10/1996 | Desai | |
| 5,569,242 A | 10/1996 | Lax et al. | |
| 5,571,100 A | 11/1996 | Goble et al. | |
| 5,584,872 A | 12/1996 | LaFontaine et al. | |
| 5,599,350 A * | 2/1997 | Schulze et al. | 606/51 |
| 5,609,151 A | 3/1997 | Mulier et al. | |
| 5,633,578 A | 5/1997 | Eggers | |
| 5,647,869 A | 7/1997 | Goble et al. | |
| 5,658,278 A | 8/1997 | Imran et al. | |
| 5,660,567 A | 8/1997 | Nierlich et al. | |

| | | | | | | |
|---|---|---|---|---|---|---|
| 5,662,680 A | 9/1997 | Desai | | 6,224,592 B1 | 5/2001 | Eggers et al. |
| 5,676,693 A | 10/1997 | LaFontaine et al. | | 6,228,078 B1 | 5/2001 | Eggers. |
| 5,681,282 A | 10/1997 | Eggers et al. | | 6,228,081 B1 | 5/2001 | Goble |
| 5,683,366 A | 11/1997 | Eggers et al. | | 6,234,178 B1 | 5/2001 | Goble et al. |
| 5,697,281 A | 12/1997 | Eggers et al. | | 6,235,020 B1 | 5/2001 | Cheng et al. |
| 5,697,536 A | 12/1997 | Eggers et al. | | 6,237,604 B1 | 5/2001 | Burnside et al. |
| 5,697,882 A | 12/1997 | Eggers et al. | | 6,238,391 B1 | 5/2001 | Olsen et al. |
| 5,697,909 A | 12/1997 | Eggers et al. | | 6,254,600 B1 * | 7/2001 | Willink et al. ................ 606/41 |
| 5,700,262 A | 12/1997 | Acosta et al. | | 6,261,286 B1 | 7/2001 | Goble et al. |
| 5,715,817 A | 2/1998 | Stevens-Wright et al. | | 6,261,311 B1 | 7/2001 | Sharkey et al. ................ 607/96 |
| 5,722,975 A | 3/1998 | Edwards et al. | | 6,264,652 B1 | 7/2001 | Eggers et al. |
| 5,725,524 A | 3/1998 | Mulier et al. | | 6,270,460 B1 | 8/2001 | McCartan et al. |
| 5,749,869 A | 5/1998 | Lindenmeier et al. | | 6,277,112 B1 | 8/2001 | Underwood et al. |
| 5,755,753 A | 5/1998 | Knowlton | | 6,280,441 B1 | 8/2001 | Ryan |
| 5,766,153 A | 6/1998 | Eggers et al. | | 6,283,961 B1 | 9/2001 | Underwood et al. |
| 5,769,847 A | 6/1998 | Panescu et al. | | 6,293,942 B1 | 9/2001 | Goble et al. |
| 5,785,705 A | 7/1998 | Baker | | 6,296,636 B1 | 10/2001 | Cheng et al. |
| 5,786,578 A | 7/1998 | Christy et al. | | 6,296,638 B1 | 10/2001 | Davison et al. |
| 5,800,429 A | 9/1998 | Edwards | | 6,308,089 B1 | 10/2001 | von der Ruhr et al. |
| 5,807,395 A | 9/1998 | Mulier et al. | | 6,309,387 B1 | 10/2001 | Eggers et al. |
| 5,810,764 A | 9/1998 | Eggers et al. | | 6,312,408 B1 | 11/2001 | Eggers et al. |
| 5,810,802 A | 9/1998 | Panescu et al. | | 6,322,549 B1 | 11/2001 | Eggers et al. |
| 5,810,809 A | 9/1998 | Rydell | | 6,355,032 B1 | 3/2002 | Hovda et al. |
| 5,836,875 A | 11/1998 | Webster, Jr. | | 6,363,937 B1 | 4/2002 | Hovda et al. |
| 5,843,019 A | 12/1998 | Eggers et al. | | 6,364,877 B1 | 4/2002 | Goble et al. |
| 5,860,951 A | 1/1999 | Eggers | | 6,379,351 B1 | 4/2002 | Thapliyal et al. |
| 5,860,974 A | 1/1999 | Abele | | 6,391,025 B1 | 5/2002 | Weinstein et al. |
| 5,860,975 A | 1/1999 | Goble et al. | | 6,409,722 B1 | 6/2002 | Hoey et al. |
| 5,871,469 A | 2/1999 | Eggers et al. | | 6,416,507 B1 | 7/2002 | Eggers et al. |
| 5,873,855 A | 2/1999 | Eggers | | 6,416,508 B1 | 7/2002 | Eggers et al. |
| 5,873,877 A | 2/1999 | McGaffigan et al. | | 6,416,509 B1 | 7/2002 | Goble et al. |
| 5,885,277 A | 3/1999 | Korth | | 6,432,103 B1 | 8/2002 | Ellsberry et al. |
| 5,888,198 A | 3/1999 | Eggers et al. | | 6,440,129 B1 | 8/2002 | Simpson |
| 5,891,095 A | 4/1999 | Eggers et al. | | 6,468,274 B1 | 10/2002 | Alleyne et al. |
| 5,891,134 A | 4/1999 | Goble et al. | | 6,468,275 B1 | 10/2002 | Wampler et al. |
| 5,897,553 A | 4/1999 | Mulier | | 6,482,201 B1 | 11/2002 | Olsen et al. |
| 5,902,272 A | 5/1999 | Eggers et al. | | 6,517,498 B1 | 2/2003 | Burbank et al. |
| 5,944,715 A | 8/1999 | Goble et al. | | 6,530,922 B2 | 3/2003 | Cosman et al. |
| 5,954,716 A | 9/1999 | Sharkey et al. | | 6,558,382 B2 * | 5/2003 | Jahns et al. ................... 606/41 |
| 5,964,786 A | 10/1999 | Ochs et al. | | 6,578,579 B2 | 6/2003 | Burnside |
| 6,004,319 A | 12/1999 | Goble et al. | | 6,589,237 B2 | 7/2003 | Woloszko et al. |
| 6,013,076 A | 1/2000 | Goble et al. | | 6,602,248 B1 | 8/2003 | Sharps et al. |
| 6,015,406 A | 1/2000 | Goble et al. | | 6,620,156 B1 | 9/2003 | Garito et al. |
| 6,024,733 A | 2/2000 | Eggers et al. | | 6,632,193 B1 | 10/2003 | Davison et al. |
| 6,027,501 A | 2/2000 | Goble et al. | | 6,632,220 B1 | 10/2003 | Eggers et al. |
| 6,039,734 A | 3/2000 | Goble et al. | | 6,749,604 B1 | 6/2004 | Eggers et al. ................ 606/41 |
| 6,047,700 A | 4/2000 | Eggers et al. | | 6,749,608 B2 | 6/2004 | Garito et al. |
| 6,056,746 A | 5/2000 | Goble et al. | | 6,770,071 B2 | 8/2004 | Woloszko et al. ............ 606/41 |
| 6,063,079 A | 5/2000 | Hovda et al. | | 6,780,178 B2 | 8/2004 | Palanker et al. |
| 6,066,134 A | 5/2000 | Eggers et al. | | 6,780,180 B1 | 8/2004 | Goble et al. |
| 6,068,628 A | 5/2000 | Fanton et al. | | 6,802,842 B2 | 10/2004 | Ellman et al. |
| 6,074,386 A | 6/2000 | Goble et al. | | 6,837,887 B2 | 1/2005 | Woloszko et al. ............ 606/41 |
| 6,090,106 A | 7/2000 | Goble et al. | | 6,837,888 B2 | 1/2005 | Ciarrocca et al. ............ 606/41 |
| 6,093,186 A | 7/2000 | Goble et al. | | 6,866,671 B2 | 3/2005 | Tierney et al. ............. 606/130 |
| 6,102,046 A | 8/2000 | Weinstein et al. | | 6,878,149 B2 | 4/2005 | Gatto ......................... 606/46 |
| 6,105,581 A | 8/2000 | Eggers et al. | | 6,890,307 B2 | 5/2005 | Kokate et al. |
| 6,109,268 A | 8/2000 | Thapliyal et al. | | 6,892,086 B2 | 5/2005 | Russell ....................... 600/372 |
| 6,117,109 A | 9/2000 | Eggers et al. | | 6,920,883 B2 | 7/2005 | Bessette et al. |
| 6,126,682 A | 10/2000 | Sharkey et al. | | 6,929,640 B1 | 8/2005 | Underwood et al. |
| 6,142,992 A | 11/2000 | Cheng et al. | | 6,949,096 B2 | 9/2005 | Davison et al. |
| 6,149,620 A | 11/2000 | Baker et al. | | 6,960,204 B2 | 11/2005 | Eggers et al. |
| 6,159,194 A | 12/2000 | Eggers et al. | | 6,974,453 B2 | 12/2005 | Woloszko et al. |
| 6,159,208 A | 12/2000 | Hovda et al. | | 6,979,601 B2 | 12/2005 | Marr et al. .................. 438/132 |
| 6,162,217 A | 12/2000 | Kannenberg et al. | | 6,984,231 B2 | 1/2006 | Goble et al. .................. 606/37 |
| 6,168,593 B1 | 1/2001 | Sharkey et al. | | 6,986,700 B2 | 1/2006 | Agarwal ......................... 451/6 |
| 6,174,309 B1 | 1/2001 | Wrublewski et al. | | 6,991,631 B2 | 1/2006 | Woloszko et al. |
| 6,179,824 B1 | 1/2001 | Eggers et al. | | 7,004,941 B2 | 2/2006 | Tvinnereim et al. |
| 6,179,836 B1 | 1/2001 | Eggers et al. | | 7,041,102 B2 | 5/2006 | Truckai et al. |
| 6,183,469 B1 | 2/2001 | Thapliyal et al. | | 7,070,596 B1 | 7/2006 | Woloszko et al. |
| 6,190,381 B1 | 2/2001 | Olsen et al. | | 7,090,672 B2 | 8/2006 | Underwood et al. |
| 6,197,021 B1 | 3/2001 | Panescu et al. | | 7,094,215 B2 | 8/2006 | Davison et al. |
| 6,203,542 B1 | 3/2001 | Ellsberry et al. | | 7,104,986 B2 | 9/2006 | Hovda et al. |
| 6,210,402 B1 | 4/2001 | Olsen et al. | | 7,131,969 B1 | 11/2006 | Hovda et al. |

| | | | |
|---|---|---|---|
| 7,169,143 B2 | 1/2007 | Eggers et al. ............. 606/32 |
| 7,179,255 B2 | 2/2007 | Lettice et al. ............. 606/32 |
| 7,186,234 B2 | 3/2007 | Dahla et al. ............... 604/22 |
| 7,192,428 B2 | 3/2007 | Eggers et al. ............. 606/41 |
| 7,201,750 B1 | 4/2007 | Eggers et al. ............. 606/41 |
| 7,217,268 B2 | 5/2007 | Eggers et al. ............. 606/32 |
| 2002/0029036 A1 | 3/2002 | Goble et al. ............... 606/38 |
| 2002/0095151 A1 | 7/2002 | Dahla et al. ............... 606/41 |
| 2003/0013986 A1 | 1/2003 | Saadat |
| 2003/0028189 A1 | 2/2003 | Woloszko et al. ......... 604/45 |
| 2003/0088245 A1 | 5/2003 | Woloszko et al. ......... 606/41 |
| 2003/0158545 A1 | 8/2003 | Hovda et al. .............. 606/32 |
| 2003/0171743 A1 | 9/2003 | Tasto et al. ................ 606/32 |
| 2003/0208194 A1 | 11/2003 | Hovda et al. .............. 606/41 |
| 2003/0208196 A1 | 11/2003 | Stone ......................... 606/41 |
| 2003/0212395 A1 | 11/2003 | Woloszko et al. ......... 606/32 |
| 2003/0212396 A1 | 11/2003 | Eggers et al. ............. 606/41 |
| 2003/0216732 A1* | 11/2003 | Truckai et al. ............. 606/49 |
| 2004/0024399 A1 | 2/2004 | Sharps et al. .............. 606/32 |
| 2004/0049180 A1 | 3/2004 | Sharps et al. .............. 606/32 |
| 2004/0054366 A1 | 3/2004 | Davison et al. ............ 606/45 |
| 2004/0116922 A1 | 6/2004 | Hovda et al. .............. 606/41 |
| 2004/0127893 A1 | 7/2004 | Hovda ........................ 606/41 |
| 2004/0153057 A1 | 8/2004 | Davison .................... 600/410 |
| 2004/0230190 A1 | 11/2004 | Dahla et al. ............... 604/41 |
| 2005/0004634 A1 | 1/2005 | Hovda et al. .............. 606/41 |
| 2005/0010205 A1 | 1/2005 | Hovda et al. .............. 606/32 |
| 2005/0033278 A1* | 2/2005 | McClurken et al. ........ 606/41 |
| 2005/0119650 A1 | 6/2005 | Sanders et al. ............ 424/426 |
| 2005/0131402 A1 | 6/2005 | Ciarrocca et al. .......... 600/450 |
| 2005/0187543 A1 | 8/2005 | Underwood et al. ....... 606/41 |
| 2005/0234439 A1 | 10/2005 | Underwood et al. ....... 606/32 |
| 2005/0251134 A1 | 11/2005 | Woloszko et al. ......... 606/32 |
| 2005/0261754 A1 | 11/2005 | Woloszko et al. ......... 606/32 |
| 2005/0288665 A1 | 12/2005 | Woloszko et al. ......... 606/41 |
| 2006/0036237 A1 | 2/2006 | Davison et al. ............ 606/41 |
| 2006/0095026 A1 | 5/2006 | Hovda et al. .............. 606/32 |
| 2006/0095032 A1 | 5/2006 | Ormsby ..................... 606/34 |
| 2006/0129145 A1 | 6/2006 | Ormsby et al. ............. 606/41 |
| 2006/0178670 A1 | 8/2006 | Woloszko et al. ......... 606/48 |
| 2006/0189971 A1 | 8/2006 | Eggers et al. ............. 606/32 |
| 2006/0253117 A1 | 11/2006 | Hovda et al. ............. 128/898 |
| 2006/0259025 A1 | 11/2006 | Dahla ........................ 607/108 |
| 2007/0010808 A1 | 1/2007 | Dahla ......................... 606/41 |
| 2007/0010809 A1 | 1/2007 | Sanders et al. ............ 606/32 |
| 2007/0161981 A1 | 7/2007 | Sanders et al. ............ 606/41 |

FOREIGN PATENT DOCUMENTS

| | | |
|---|---|---|
| EP | 0703461 A2 | 3/1996 |
| EP | 0740926 A2 | 11/1996 |
| EP | 0 754 437 | 1/1997 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 12/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | 2/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 00/000098 | 1/2000 |
| WO | 00/009053 | 2/2000 |
| WO | 01/87154 | 5/2001 |
| WO | 02/102255 | 2/2002 |
| WO | 02/36028 | 5/2002 |
| WO | 03/024305 | 3/2003 |
| WO | 03/092477 | 11/2003 |
| WO | 04/071278 | 8/2004 |
| WO | 05/125287 | 12/2005 |
| WO | 07/006000 | 1/2007 |
| WO | 07/056729 | 5/2007 |

OTHER PUBLICATIONS

Pearce, John A. "Electrosurgery", pp. 17, 69-75, 87, John Wiley & Sons, New York.

J.W. Ramsey et al., "A Comparison of Bipolar and Monopolar Diathermy Probes in Experimental Animals", *Urological Research* vol. 13, pp. 99-102.

V.E. Elsasser et al., "An Instrument for Transurethral Resection without Leakage of Current" *Acta Medicotechnica* vol. 24, No. 4, pp. 129-134.

P.C. Nardella *SPIE* 1068:42-49 Radio Frequency Energy and Impedance Feedback

R. Tucker et al., Abstract P14-11, p. 248, "A Bipolar Electrocurgical Turp Loop".

R. Tucker et al. "A Comparison of Urologic Application of Bipolar Versus Monopolar Five French Electrosurgical Probes" *J. of Urology* vol. 141, pp. 662-665.

R. Tucker et al. "In Vivo effect of 5 French Bipolar and Monopolar Electrosurgical Probes on the Porcine Bladder" *Urological Research* vol. 18, pp. 291-294.

Kramolowsky et al. "Use of 5F Bipolar Electrosurgical Probe in Endoscopic Urological Procedures" *J. of Urology* vol. 143, pp. 275-277.

Kramolowsky et al. "The Urological App. of Electrosurgery" *J. of Urology* vol. 146, pp. 669-674.

Slager et al. "Spark Erosion of Arteriosclerotic Plaques" *Z. Kardiol.* 76:Suppl. 6, 67-71.

Slager et al. "Vaporization of Atherosclerotice Plaques by Spark Erosion" *JACC* 5(6):1382-6.

Olsen MD, Bipolar Laparoscopic Cholecstectomy Lecture (marked confidential), 12 pgs.

Codman & Shurtleff, Inc. "The Malis Bipolar Electrosurgical System CMC-III Instruction Manual", 15 pgs.

Valley Forge's New Products, CLINICA, 475, 5.

Valley Forge Scientific Corp., "Summary of Safety and Effective Information from 510K", 2pgs.

Codman & Shurtleff, Inc. "The Malis Bipolar Coagulating and Bipolar Cutting System CMC-II" brochure, earl, 2pgs.

L. Malis, "The Value of Irrigation During Bipolar Coagulation" See ARTC 21602, 1 pg.

L. Malis, "Excerpted from a seminar by Leonard I. Malis, M.D. at the 1995 American Association of Neurological Surgeons meeting," 1pg.

L. Malis, "Electrosurgery, Technical Note," *J. Neursurg.*, vol. 85, 970-975, Nov. 1996.

Ian E. Shuman, "Bipolar Versus Monopolar Electrosurgery: Clinical Applications," *Dentistry Today*, vol. 20, No. 12, 7 pgs.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455.

Cook et al., "Therapeutic medical Devices: Application and Design", Prentice Hall, Inc., 3pgs.

Valleylab SSE2L Instruction Manual, 11 pgs.

Robert D. Tucker et al., "Demodulated Low Frequency Currents from Electrosurgical Procedures," *Surgery, Gynecology and Obstetrics*, 159:39-43.

Lu, et al., "Electrical Thermal Angioplasty: Catheter Design Features, In Virto Tissue Ablation Studies and In Vitro Experimental Findings," *Am J. Cardiol* vol. 60, pp. 1117-1122.

Selikowitz et al., "Electric Current and Voltage recordings on the Myocardium During Electrosurgical Pricedures in Canines," *Surgery, Gynecology & Obstetrics*, vol. 164, 219-224.

J. O'Malley, Schaum's Outline of Theory and Problems of Basic Circuit Analysis, McGraw-Hill, 2nd Ed., pp. 3-5.

Arnaud Wattiez et al., "Electrosurgery in Operative Endoscopy," Electrosurgical Effects, Blackwell Science, pp. 85-93.

Leslie A. Geddes, "Medical Device Accidents: With Illustrative Cases" CRC Press, 3 pgs.

Wyeth, "Electrosurgical Unit" pp. 1181-1202.

C.P. Swain, et al., "Which Electrode, A Comparison of four endoscopic methods of electrocoagulation is experimental bleeding ulcers" *GUT* vol. 25, pp. 1424-1431.

Piercey et al., "Electrosurgical Treatment of Experimental Bleeding Canine Gastric Ulcers" *Gastroenterology* vol. 74(3), pp. 527-534.

A.K. Dobbie, "The Electrical Aspects of Surgical Diathermy, Bio Medical Engineering" *Bio-Medical Engineering* vol. 4, pp. 206-216.

B. Lee et al. "Thermal Compression and Molding of Artherosclerotic Vascular Tissue with Use" JACC vol. 13(5), pp. 1167-1171.

K. Barry et al., "The Effect of Radiofrequency-generated Thermal Energy on the Mechanical and Histologic Characteristics of the Arterial Wall In Vitro: Implications of Radiofrequency Angioplasty" *American Heart Journal* vol. 117, pp. 332-341.

W. Honig, "The Mechanism of Cutting in Electrosurgery" *IEEE* pp. 58-65.

Pearce, John C., "Electrosurgery", Handbook of Biomedical Engineering, chapter 3, Academic Press Inc., N.Y., pp. 98-113.

M.B. Dennis et al. "Evolution of Electrofulguration in Control of Bleeding of Experimental Gastric Ulcers," Digestive Diseases and Sciences, vol. 24, No. 11, 845-848.

Letter from Department of Health to Jerry Malis dated Jul. 25, 1985, 1 pg.

Letter from Jerry malis to FDA dated Jul. 25, 1985, 2 pgs.

Letter from Department of Health to Jerry Malis dated Jan. 24, 1991, 3 pgs.

Leonard Malis, "Instrumentation of Microvascular Neurosurgery" *Cerebrovascular Surgery*, vol. 1, 245-260.

Valleylab, Inc. "Valleylab Part No. 945 100 102 A" Surgistat Service Manual, pp. 1-46.

Leonard I. Malis, "New Trends in Microsurgery and Applied Technology," *Advanced Technology in Neurosurgery*, 1-16.

Buchelt, et al. "Excimer Laser Ablation of Fibrocartilage: An In Vitro and In Vivo Study", Lasers in Surgery and Medicine, vol. 11, pp. 271-279.

Costello et al., "Nd: YAG Laser Ablation of the Prostate as a Treatment for Benign Prostatic Hypertrophy", lasers in Surgery and Medicine, vol. 12, pp. 121-124.

Rand et al., "Effect of Elecctrocautery on Freash Human Articular Cartilage", J. Arthro. Surg., col. 1, pp. 242-246.

PCT International Search Report for PCT/US99/14685 (Atty docket No. CB-01PC), 1 pg.

PCT Notification of International Preliminary Examination Report for PCT/US99/14685 (Atty docket No. CB-01PC), 4 pgs.

PCT International Search Report for PCT/US98/22323 (Atty docket No. CB-02PC), 1 pg.

PCT Notification of International Preliminary Examination Report for PCT/US98/22323 (Atty docket No. CB-02PC), 5 pgs.

European Search Report for EP 98953859 (Atty docket No. CB-02EP), 2 pgs.

Supplementary European Search Report for EP 98953859 (Atty docket No. CB-02EP), 3 pgs.

PCT International Search Report for PCT/US99/18289 (Atty docket No. CB-07PC), 1 pg.

PCT Notification of International Preliminary Examination Report for PCT/US99/18289 (Atty docket No. CB-07PC), 4 pgs.

European Search Report for Ep 99945039.8 (Atty docket No. CB-07EP), 3 pgs.

PCT International Search Report for PCT/US02/19261 (Atty docket No. CB-11-1), 1 pg.

PCT International Preliminary Examination Report for PCT/US02/19261 (Atty docket No. CB-11-1), 3 pgs.

PCT International Search Report for PCT/US02/29476 (Atty docket No. CB-12), 1 pg.

PCT International Search Report for PCT/US03/13686 (Atty docket No. CB-14), 1 pg.

PCT International Search Report for PCT/US04/03614 (Atty docket No. CB-16), 1 pg.

PCT Written Opinion of the International Searching Authority for PCT/US04/03614 (Atty docket No. CB-16), 4 pgs.

EP Communication, European Examination Report for EP 98953859.0 (Atty docket No. CB-02EP), 3 pgs.

EP Communication, European Examination Report for EP 99945039.8 (Atty docket No. CB-07EP), 5 pgs.

Stoffels, E. et al., "Investigation on the Interaction Plasma-Bone Tissue", E-MRS Spring Meeting, 1 pg.

Stoffels, E. et al., "Biomedical Applications of Plasmas", Turotial present prior to the 55th Gaseous Electronics Conference in Minneapolis, MN, 41 pgs.

Stoffels, E. et al., "Plasma Interactions with Living Cells", Eindhoven University of Technology, 1 pg.

Stoffels, E. et al., "Superficial Treatment of Mammalian Cells using Plasma Needle", J. Phys. D: Appl. Phys. 26, pp. 2908-2913.

Stoffels, E. et al., "Plasma Needle", Eindhoven University of Technology, 1 pg.

Stoffels, E. et al., "Plasma Physicists Move into Medicine", Physicsweb, 1 pg.

Stoffels, E. et al., "Plasma Treated Tissue Engineered Skin to Study Skin Damage", Biomechanics and Tissue Engineering, Materials Technology, 1 pg.

Stoffels, E. et al., "Plasma Treatment of Dental Cavities: A Feasibility Study", IEEE Transaction on Plasma Science, vol. 32, No. 4, pp. 1540-1542.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550.

Stoffels, E. et al., "Electrical and Optical Characterization of the Plasme Needle", New Journal of Physics 6, pp. 1-14.

Stoffels, E. et al., "Where Plasma Meets Plasma", Eindhoven University of Technology, 23 pgs.

Stoffels, E. et al., "Gas Plasma effects on Living Cells", Physics Scripta, T107, pp. 79-82.

Stoffels, E. et al., "Plasma Treatment of Mammalian Vascular Cells: A Quantitative Description", IEEE Transaction on Plasma Science, vol. 33, No. 2, pp. 771-775.

Stoffels, E. et al., "Deactivation of Escherichia Coli by the Plasma Needle", J. Phys. D: Appl. Phys. 38, pp. 1716-1721.

Stoffels, E. et al., "Development of a Gas Plasma Catheter for Gas Plasma Surgery", XXVIIth ICPIG, Endoven University of Technology, pp. 18-22.

Stoffels, E. et al., "Development of a Smart Positioning Sensor for the Plasma Needle", Plasma Sources Sci. Technol. 15, pp. 582-589.

Stoffels, E. et al., Killing of S. Mutans Bacteria Using a Plasma Needle at Atmospheric Pressure, IEEE Transaction on Plasma Science, vol. 34, No. 4, pp. 1317-1324.

Stoffels, E. et al., "Plasma-Needle Treatment of Substrates with Respect to Wettability and Growth of Excherichia Coli and Streptococcus Mutans", IEEE Transaction on Plasma Science, vol. 34, No. 4, pp. 1325-1330.

Stoffels, E. et al., "Reattachment and Apoptosis after Plasma-Needle Treatment of Cultured Cells", IEEE Transaction on Plasma Science, vol. 34, No. 4, pp. 1331-1336.

Stoffels, E. et al., "UV Excimer Lamp Irradiation of Fibroblasts: The Influence on Antioxident Homostasis", IEEE Transaction on Plasma Science, vol. 34, No. 4, pp. 1359-1364.

Stoffels, E. et al., "Plasma Needle for In Vivo Medical Treatment: Recent Developments and Perspectives", Plasma Sources Sci. Technol. 15, pp. S169-S180.

PCT Notification of International Search Report and Written Opinion for PCT/US06/26321 (Atty docket No. CB-17PC), 8pgs.

* cited by examiner

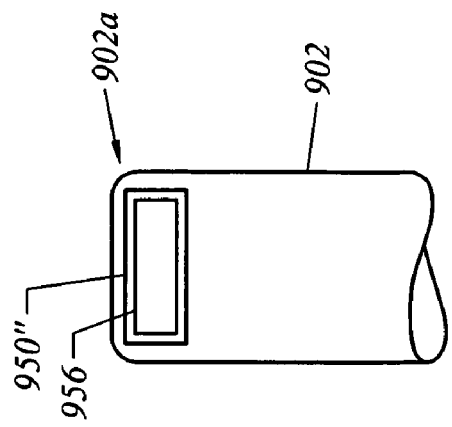
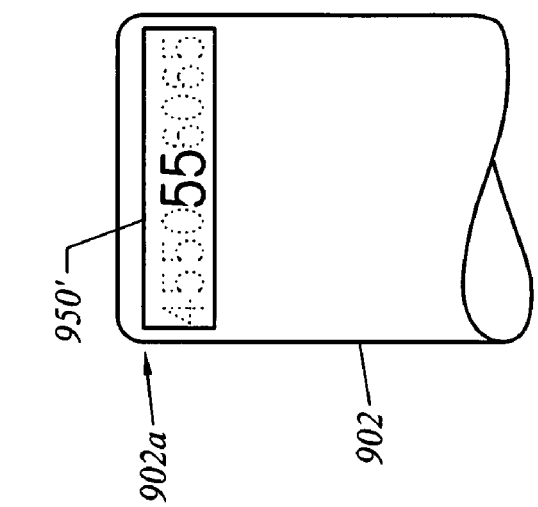
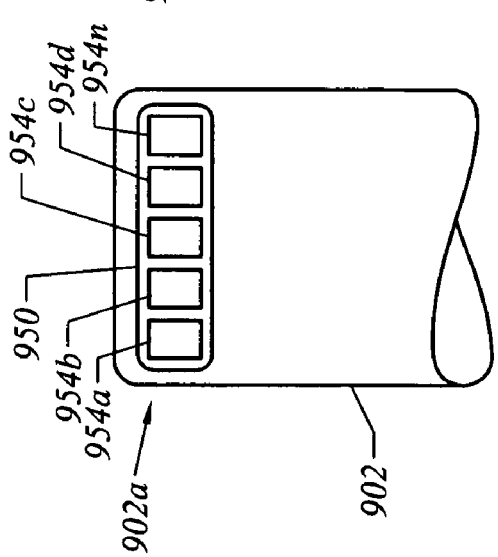
FIG. 9C
FIG. 9B
FIG. 9A

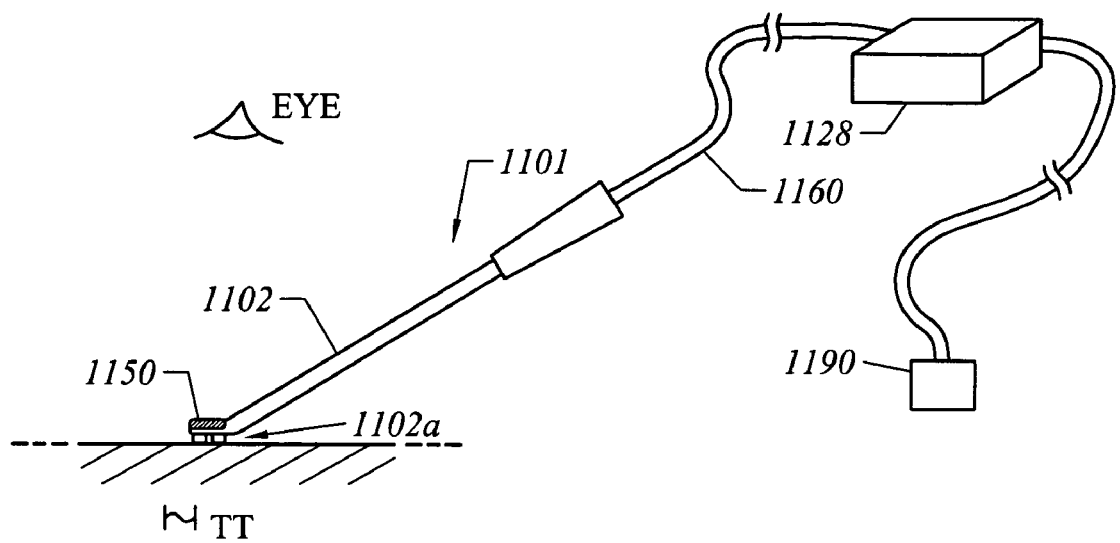
*FIG. 11A*
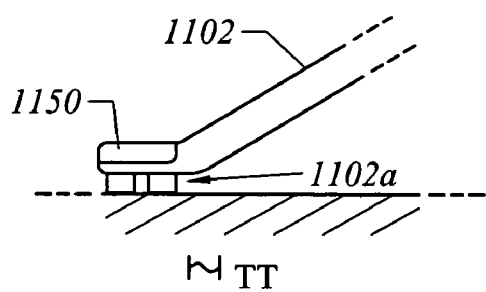 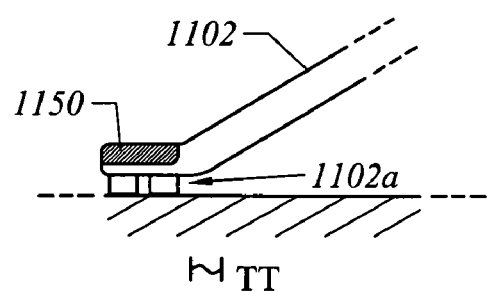
*FIG. 11B*        *FIG. 11C*

TEMPERATURE INDICATING ELECTROSURGICAL APPARATUS AND METHODS

This application claims the benefit of U.S. Ser. No. 60/445,405 filed Feb. 5, 2003.

BACKGROUND OF THE INVENTION

The present invention relates generally to the field of electrosurgical devices, and more particularly to methods and devices allowing for the monitoring of temperature in regions adjacent, in contact with, and/or surrounding a working end of such electrosurgical devices.

Electrosurgical procedures are extremely common in today's medical practice. For example, present uses of electrosurgical devices include ablation, dissection, resection, coagulation, contraction, or otherwise modification of a broad range of tissues and organs. Thus, general surgery, cosmetic surgery, neurosurgery, laparoscopy, as well as arthroscopic procedures, etc., routinely employ electrosurgical devices and techniques. However, unintended and excessive heating of non-target tissue during the procedure is a common concern in most electrosurgical applications. Such unintended heating of non-target tissue may cause inadvertent necrosis or other damage. Naturally, a medical practitioner employing such devices has a need to know the temperature of the region adjacent to, surrounding, and/or in contact with the working end of the device.

Most electrosurgical cutting devices operate by applying electrical energy to affect tissue. In a first mode, electrical current flows through tissue and as a result of a high current density at the working end of the electrosurgical device (e.g., an electrode), an electrical arc forms across a gap between the electrode and the target tissue. The arc results in rapid tissue heating and vaporization of cellular fluids into steam. In another mode, electrical energy may be directly conducted through tissue, but instead of forming an arc, the resistive properties of the tissue result in heating of the tissue to produce a thermal effect. In yet another mode, as developed by ArthroCare Corporation, Sunnyvale Calif., RF energy is applied to a conductive medium (usually saline), causing a highly focused plasma field to form around the electrodes. This plasma field is comprised of highly ionized particles which have sufficient energy to break organic molecular bonds within tissue. The by-products of this non-heat driven process are elementary molecules and low molecular weight gases. This latter mode is a non-heat driven (the ablation is achieved via the ionized particles) low temperature (surface tissue temperatures 40–70° C.) ablative process and is termed Coblation®. The Coblation® process is discussed more thoroughly below.

In all of the modes described above, a certain amount of heat is generated in the tissue as either a by-product or as a direct result of the mode. This heat conducts through tissue. In the modes which rely on passing electrical current through tissue, electrical current as well as heat conduct through tissue. As a result, heating often occurs not only in or near the target tissue but also in regions surrounding the target tissue. Accordingly, such heating of the surrounding tissue may result in undesirable collateral tissue damage.

Another problem may be found as some surgical procedures require a "wet" field, (i.e., the surgical site is immersed in a fluid medium.) Heat generated by the electrosurgical procedure may accumulate in the fluid medium through transfer of heat into the fluid. In those cases where the fluid medium is a electrically conductive, shorting of the electrode(s) may also occur and result in additional unintended heating in the treatment area. Ultimately, too much additional heating may result in excessive collateral tissue damage.

A number of electrosurgical devices are known that include temperature sensors for sensing temperature in or around a surgical site during a procedure. Such devices typically use electrical temperature sensors, such as thermistors, thermocouples, resistance temperature detectors (RTDs), or fiber optic-based temperature sensors (e.g., U.S. Pat. Nos. 6,293,943 and 6,197,021, both to Panescu et al.).

However, during the procedures described above, a medical practitioner's attention is mainly focused on the operative field either through a viewing monitor (e.g., during a less invasive procedure) or direct visualization (e.g., an open surgical procedure.) Accordingly, there remains a need remains for the medical practitioner to be able to identify the temperature in regions adjacent to, in contact with, and/or surrounding a working end of a electrosurgical devices without solely having to remove his or her attention from the operative field. There also remains a need to provide such a medical device that is disposable and compatible with existing controllers or power supplies.

SUMMARY OF THE INVENTION

The present invention provides systems, devices, and methods for the monitoring of temperature in regions adjacent, in contact with, and/or surrounding an electrosurgical device.

The invention includes a device having an energy delivery assembly comprising at least one energy delivery element. The device will be coupled to an energy delivery unit. In the operative area of the device, or at any portion of the device that would intersect a patient, the device will include at least one temperature indicating element that gives the medical practitioner or operator of the device a visual indication that a particular temperature adjacent to the device is reached. The device may have one or more temperature-indicating elements, each having one or more activation-temperature ranges.

The temperature-indicating element may be reversible, that is it may give a real-time indication of the temperature adjacent to the element. For example, as the area around the element increases in temperature, the element will give a visual indication upon reaching an initial activation temperature. When the surrounding area cools, the temperature indicating element will revert to its natural state. Alternatively, the temperature indicating element may give an irreversible indication of the temperature adjacent to the element.

One variation of the invention includes an electrosurgical device generally having an elongated shaft having proximal and distal end portions, at least one active electrode disposed on the elongated shaft for applying energy to a patient's tissue, one or more connectors for coupling the active electrode to a source of high frequency electrical energy (e.g., an electrosurgical generator or power supply) and at least one temperature-indicating element which is readily visible to the operator of the device during a procedure. The device typically further includes a return electrode, spaced from the active electrode(s). The temperature-indicating element(s) may be exposed on or conforms to an external surface of the shaft. Typically, the temperature-indicating element is located at a working end of the shaft and/or may be located along any portion or portions of the device where information regarding surrounding temperature is desired.

The temperature-indicating element may include a thermochromic composition, such as an ink, paint, film, sheet, etc., formulated to undergo a visibly apparent transition at one or more pre-defined temperatures. For example, in the many electrosurgical procedures contemplated under the invention the one or more pre-defined temperatures are typically in the range of from about 40° C. to 95° C. The pre-defined temperature at which the temperature-indicating element undergoes a thermochromic transition may vary, e.g., according to the procedure, e.g., the nature of the target tissue (bone, cartilage, skin), and the intended effect of treatment (ablation, coagulation, contraction). The temperature-indicating element may also include a separate element that incorporates the thermochromatic/thermochromic composition.

In certain embodiments of the invention, a temperature-indicating element may comprise a thermochromic composition that may be applied, or affixed, to the shaft of a device over a temperature indicator base or pad. Such a temperature indicator base may serve to attach the temperature-indicating element to the shaft. Alternatively, or additionally, the base may thermally or electrically insulate the temperature-indicating element from other components of the device. Alternatively, or in combination, the temperature indicating elements may be directly applied, placed, attached, etc. to the device.

In one embodiment, the temperature-indicating element may comprise an annular band (e.g., rubber, plastic, ceramic, composite, etc. material) having a thermochromic material incorporated therewith. Such an annular band may encircle the shaft distal end portion. Alternatively, or in combination, the temperature element may simply be the thermochromic material placed directly upon the device with or without an intermediate layer. In one embodiment, the temperature-indicating element is encased within a biocompatible sheath. The sheath may be colored or colorless, and may itself comprise a thermochromic material. Such a thermochromic sheath may undergo a visual transition, e.g., from opaque to translucent or transparent (or reverse), as it approaches a pre-defined temperature.

According to another embodiment of the invention, the temperature-indicating element comprises a plurality of thermochromic cells, each of the cells having a thermochromic composition. The thermochromic composition of each cell may be formulated or adapted to sequentially undergo a visual transition at successively higher temperatures, whereby a rising temperature condition at the shaft distal end portion can be monitored by visual examination of one or more of the thermochromic cells. In one embodiment, the cells of the temperature-indicating element may sequentially display a different temperature value as the temperature changes.

In another embodiment, a temperature indicating element of an electrosurgical device includes a message unit which is adapted to display an alpha-numeric message, temperature data, or the like, in response to a pre-defined temperature condition at the shaft distal end portion of the device.

In one aspect, the present invention provides a method of visually monitoring a temperature condition at a surgical site during an electrosurgical procedure, wherein the method comprises providing an electrosurgical device having a temperature indicating element at the working end of the device, and observing the temperature-indicating element for a change in appearance of the temperature-indicating element. The appearance of the temperature-indicating element may provide a signal to the user of the device of a temperature condition near the working end of the device. Accordingly, the user may adjust settings, decrease the energy supplied to the device, or shut off the device, according to the appearance of the temperature-indicating element.

According to another embodiment of the invention, there is provided a method of monitoring a temperature at a surgical site prior to, or during, a procedure to be performed using an electrosurgical device.

Another variation of the invention includes a medical device for use with an energy delivery unit, comprising a shaft having a shaft distal end portion and a shaft proximal end portion, an energy delivery assembly comprising at least one energy delivery element disposed near the shaft distal end portion and adapted to be coupled to the energy delivery unit; a connector fixedly engaged to the shaft proximal end portion adapted to couple the device to the energy delivery unit; and a first means for providing a visually indication of a particular temperature or range of temperatures in a region adjacent a portion of the shaft. Where the means for providing a visual indication of temperatures is the temperature-indicating elements described herein.

The temperature-indicating elements of the present invention may be combined with electrosurgical devices (such as bi-polar and monopolar devices as described in detail below) and with other devices that deliver energy. For example, the invention includes, but is not limited to ultrasound, mechanical, laser, thermal, microwave, chemical, and radiation, etc. energy devices.

In other embodiments, a temperature-indicating element separate from the electrosurgical device, e.g., disposed on a temperature probe, may be positioned at the surgical site prior to, or during, a procedure, and the temperature may be visually monitored according to the appearance of one or more thermochromic materials of the temperature-indicating element.

These and other features of the invention will become apparent to those persons skilled in the art upon reading the details of the invention as more fully described below.

BRIEF DESCRIPTION OF THE DRAWINGS

FIG. 6F is a plan view of the device of FIG. 6E taken along the lines 6F—6F;

FIGS. 9A–C each schematically represent a temperature-indicating element disposed on a distal end portion of a shaft of an electrosurgical device, according to three different embodiments of the instant invention;

FIGS. 11A–C schematically represent a visual change of a temperature-indicating element of a device during a surgical procedure, according to the invention;

DESCRIPTION OF SPECIFIC EMBODIMENTS

Figure 1:
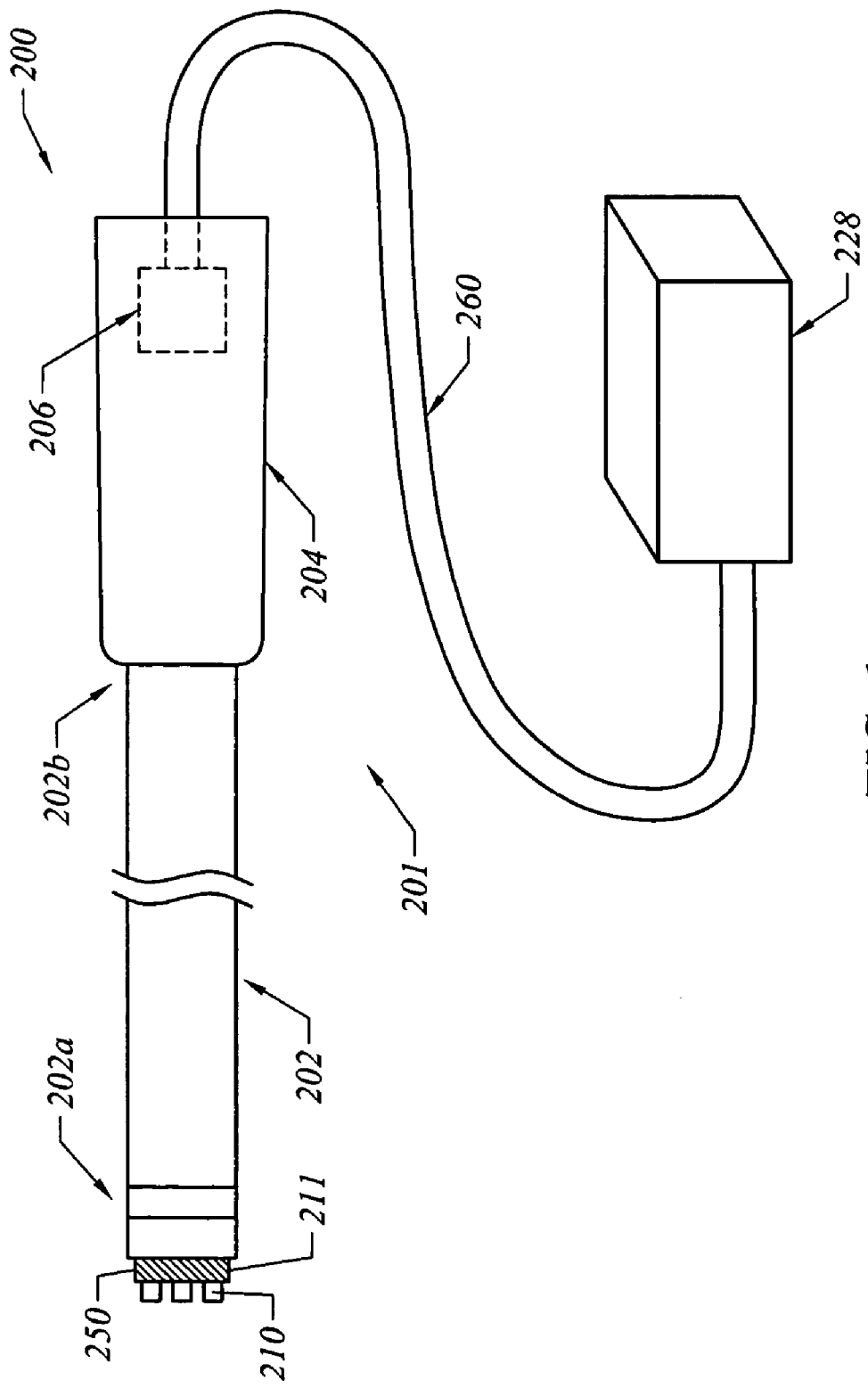
FIG. 1 illustrates a system including an electrosurgical probe, the probe having a temperature indicating element according to one embodiment of the invention.

The present invention provides systems, apparatus, and methods for selectively applying energy to a target tissue of a patient, and for monitoring a temperature condition in the region of the target tissue and/or at the working end of an device adapted for such application of energy. The invention is particularly suited to the facile and convenient monitoring of a temperature condition at the working end of an device during an electrosurgical procedure, wherein the temperature may be monitored simply by observing a readily apparent change in the appearance of a temperature indicating element. Such a temperature-indicating element may be integral with the device. The temperature-indicating element is typically disposed at the working end of the device at a location where it is easily viewed by a member of the surgical team during a procedure.

It is to be understood that the application of the present invention is not necessarily limited to electrosurgical devices, or plasma-assisted electrosurgical devices. Rather, the present invention may have applications in any energy delivery surgical device (e.g., laser, ultrasound, resistive heating, microwave, chemical, etc.) For purposes of illustration, the variations of the invention are discussed in relation to electrosurgical devices and plasma assisted electrosurgical devices.

Systems, apparatus, and methods of the invention are applicable to a broad range of procedures, including: open procedures, intravascular procedures, urological procedures, laparoscopy, arthroscopy, cardiac procedures (including thoracoscopy), dermatologic, orthopedic, gynecological, otorhinolaryngological, spinal, and neurologic procedures, as well as in oncology, and the like. Tissues which may be treated by apparatus and methods of the present invention include, without limitation, connective tissue, including bone and cartilage; prostate tissue; leiomyomas (fibroids) of the uterus; gingival tissues and mucosal tissues of the mouth; tumors; scar tissue; and myocardial tissue; as well as collagenous tissue of the eye, and the dermis and epidermis of the skin.

The present invention is useful for arthroscopic procedures of the knee, shoulder, elbow, etc., including the ablation, re-shaping, or re-surfacing of articular cartilage, and the partial removal or modification of a damaged meniscal cartilage of the knee. The invention is also applicable to a broad range of spinal procedures, including without limitation, laminectomy/discectomy procedures for treating herniated disks, posterior lumbosacral and cervical spine fusions, treatment of scoliosis associated with vertebral disease, and foraminotomies to relieve nerve root compression.

The present invention is also useful for procedures in the head and neck, e.g., targeting the ear, mouth, pharynx, larynx, esophagus, nasal cavity and sinuses. These procedures may be performed through the mouth or nose using speculae or gags, or using endoscopic techniques, such as functional endoscopic sinus surgery (FESS). The present invention may also be used for collagen shrinkage, ablation, and/or hemostasis, e.g., during procedures for treating snoring and obstructive sleep apnea; for gross tissue removal, such as tonsillectomies, adenoidectomies, tracheal stenosis and vocal cord polyps and lesions; or for the resection or ablation of facial tumors or tumors within the mouth and pharynx, such as glossectomies, laryngectomies, acoustic neuroma procedures, and nasal ablation procedures.

Apparatus and methods of the present invention may also be useful for cosmetic and plastic surgery procedures. For example, the present invention may be employed for skin tissue removal and/or collagen shrinkage in the epidermis or dermis of the head and neck, e.g., the removal of pigmentations, vascular lesions, scars, tattoos, etc., as well as for other surgical procedures on the skin, such as tissue rejuvenation, cosmetic eye procedures (blepharoplasties), wrinkle removal, tightening muscles for facelifts or brow-lifts, hair removal and/or transplant procedures, etc.

As noted above, although the present invention may be applied to any type of electrosurgical device, including those using (RF) energy, the device is particularly useful in those devices using Coblation® technology (plasma assisted electrosurgical ablation devices).

Coblation® requires application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive medium over at least a portion of the active electrode(s) in the region between the distal tip of the active electrode(s) and the target tissue. The electrically conductive medium may be, for example, a liquid, gel or gas. Such electrically conductive medium include isotonic saline, blood, extracellular or intracellular fluid, delivered to, or already present at, the target site, or a viscous medium, such as a gel, applied to the target site.

When the conductive medium is heated enough such that atoms vaporize off the surface faster than they recondense, a gas is formed. When the gas is sufficiently heated such that the atoms collide with each other and knock their electrons off in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882 the complete disclosure of which is incorporated herein by reference.

In some applications of the Coblation technology, high frequency (RF) electrical energy is applied in an electrically conducting media environment to shrink or remove (i.e., resect, cut, or ablate) a tissue structure and to seal transected vessels within the region of the target tissue. Coblation technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue. In other applications, an electrosurgical instrument is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. A single voltage can be applied to the tissue by the coagulation electrode(s), as well as to the active electrode(s) to ablate or shrink the tissue. In certain applications, the power supply is combined with the coagulation instrument such that the coagulation electrode is used when the power supply is in the coagulation mode (low voltage), and the active electrode(s) are used when the power supply is in the ablation mode (higher voltage).

The amount of energy produced by the Coblation® technology may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the medium in contact with the electrodes; density of the medium; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue, (e.g., adipose) tissue has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032, 6,149,120 and 6,296,136, the complete disclosures of which are incorporated herein by reference.

The active electrode(s) of a Coblation® device are preferably supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

While Coblation® ablates tissue in a non-thermal manner, surface temperature of the tissue has been observed to be in the range of 40–70° C. Accordingly, it still may be desirable for the medical practitioner to have the ability to directly observe the temperature environment of the surgical site when using a Coblation® device. However, it is noted that the invention described herein may be applied to any type of surgical instrument which generates heat either directly, or as a by-product of the procedure. For example, the invention may be incorporated in devices using microwave energy, laser, UV light based, mechanical energy, etc. It is noted that the device has particular value in thermal electrosurgical devices.

In one embodiment of the present invention, radio frequency (RF) electrical energy is applied to one or more active electrodes of a device in the presence of an electrically conductive fluid, to remove and/or modify at least a portion of a target tissue or organ. Depending on the specific procedure, the present invention may be used to: (1) ablate (i.e., volumetrically remove or effect the molecular dissociation of) tissue, including soft tissue, bone, and cartilage;

(2) cut or resect tissue; (3) shrink or contract collagen containing tissue; and/or (4) coagulate, occlude, and sever blood vessels.

An electrosurgical device of the invention typically includes a shaft having a proximal end and a distal or working end portion, and one or more active electrodes at the shaft distal end portion. In some embodiments, the active electrode(s) will be disposed at the distal tip or apex of the device. Alternatively or additionally, the active electrode(s) may be formed on lateral surfaces of the shaft (e.g., for facilitating access to a target tissue in certain procedures). A return electrode is typically spaced from the active electrode(s) by an electrically insulating electrode support or spacer.

The shaft may assume a wide variety of configurations. The shaft mechanically supports the active electrode(s), and enables the treating physician or surgeon to manipulate the active electrode(s) from the proximal end of the device. The shaft may be linear, variously curved, rigid, malleable or flexible. Flexible shafts may be combined with pull wires, shape memory actuators, or other known mechanisms for effecting selective deflection of the distal end of the shaft to facilitate positioning of the shaft distal end/active electrode(s) with respect to the target tissue.

Typically, devices of the invention are adapted for coupling to an electrosurgical generator incorporating a RF power supply, wherein the power supply is capable of operation in an ablation mode (for ablating tissue), or a sub-ablation mode (for coagulating or otherwise modifying the tissue). Typically, electrosurgical devices of the invention will include one or more electrode leads by which the electrode(s) are connected to a connection block. The connector is adapted for coupling the electrode(s) to the generator or power supply. Typically, the connector includes a plurality of pins for coupling to the power supply via a connector cable.

Devices of the invention may use a single active electrode or an electrode array distributed over a working end of the device. In the latter embodiment, the electrode array may include a plurality of independently current-limited and/or power-controlled active electrodes to apply electrical energy selectively to the target tissue while limiting the unwanted application of electrical energy to the surrounding tissue and environment. In one configuration, each individual active electrode in the electrode array is electrically insulated from all other active electrodes in the array, and each active electrode is connected to a power source which is isolated from each of the other active electrodes in the array, or to circuitry which limits or interrupts current flow to the active electrode when low resistivity material (e.g., blood, saline) causes a lower impedance path between the return electrode and the particular active electrode. Apparatus incorporating independently current-limited and/or power-controlled active electrodes is described in commonly assigned U.S. Pat. No. 6,312,408, the disclosure of which is incorporated by reference herein in its entirety.

It should be clearly understood that the invention is not limited to electrically isolated active electrodes, or even to a plurality of active electrodes. For example, the array of active electrodes may be connected to a single lead that extends through the probe shaft to a source of high frequency current. In one embodiment, the probe may have only a single active electrode that extends from an insulating spacer at the probe distal end. The active electrode(s) may have a ball shape (e.g., for tissue vaporization and desiccation), a twizzle shape (for vaporization and needle-like cutting), a spring shape (for rapid tissue debulking and desiccation), a twisted metal shape, an annular or solid cylindrical shape, or various other regular or irregular shapes.

The voltage applied between the active and return electrodes will typically be in the radio frequency (RF) range, having a frequency between about 5 kHz and 20 MHz, usually being between about 30 kHz and 2.5 MHz, and often between about 100 kHz and 200 kHz. The RMS (root mean square) voltage applied will usually be in the range from about 5 volts RMS to 1500 volts RMS, typically being in the range of from about 10 volts RMS to 900 volts RMS, and often in the range of from about 20 volts RMS to 500 volts RMS, depending on the active electrode size and geometry, the operating frequency, and the particular procedure or desired effect on the tissue (e.g., ablation, contraction, coagulation). Typically, the peak-to-peak voltage will be in the range of 10 to 2000 volts, usually in the range of 20 to 1200 volts, and often in the range of about 40 to 800 volts (again, depending on the electrode size, the operating frequency, and the operation mode). Voltage parameters for various electrosurgical procedures are presented in commonly assigned U.S. Pat. No. 6,235,020, the disclosure of which is incorporated by reference herein in its entirety.

The voltage is typically delivered in a series of voltage pulses or alternating current of time varying voltage amplitude having a sufficiently high frequency (e.g., on the order of 5 kHz to 20 MHz) such that the voltage is effectively applied continuously (as compared with, e.g., certain lasers adapted for shallow depths of tissue necrosis, which are generally pulsed at about 10 Hz to 20 Hz). In addition, the duty cycle (i.e., cumulative time in any one-second interval that energy is applied) is on the order of about 50% for apparatus of the present invention, as compared with a duty cycle of about 0.0001% for many pulsed lasers.

The application of a suitable high frequency voltage between the active and return electrodes effects cutting, removal, ablation, shaping, contracting, coagulating, or other form of modification of the target tissue. The tissue volume over which energy is dissipated may be precisely controlled, for example, by the use of a multiplicity of small active electrodes whose effective diameters or principal dimensions typically range from about 5 mm to 0.01 mm, and usually from about 2 mm to 0.05 mm. In these embodiments, electrode areas for both circular and non-circular electrode terminals will have a contact area (per active electrode) of 25 mm2 or less, typically being in the range from 5 mm2 to 0.005 mm2. In general, the use of relatively small diameter active electrodes increases the electric field intensity, and reduces the extent or depth of tissue heating as a consequence of the divergence of current flux lines which emanate from the exposed surface of each active electrode.

A preferred power supply of the present invention delivers a high frequency current selectable to generate average power levels ranging from several milliwatts to tens of watts per electrode, depending on the volume of target tissue being treated, and/or the maximum allowed temperature selected for the probe tip. The power supply allows the user to select the voltage level according to the specific requirements of a particular procedure, e.g., FESS procedure, dermatological procedure, ophthalmic procedure, arthroscopic surgery or other endoscopic surgery, or open surgery. A description of a power supply adapted for electrosurgery can be found in commonly assigned U.S. Pat. No. 6,142,992, the disclosure of which is incorporated by reference herein in its entirety.

A current flow path between the active and return electrodes may be provided by delivering an electrically conductive fluid (e.g., an electrically conductive gel or saline) to the working end of the device. To provide a suitable current flow path between the active and return electrodes, an electrically conductive fluid delivered to the working end of the device should have a suitable electrical conductivity, typically at least 0.2 millisiemens per centimeter (mS/cm), usually greater than 2 mS/cm, and often greater than 10 mS/cm. In one embodiment, the electrically conductive fluid is isotonic saline, which has a conductivity of about 17 mS/cm. In other embodiments, electrically conductive fluids having electrical conductivity values much higher than that of isotonic saline may also be used. A discussion of various electrically conductive fluids, having a range of electrical conductivity values, suitable for use in electrosurgery appears in commonly assigned U.S. Pat. No. 6,149,620, the disclosure of which is incorporated by reference herein in its entirety. Delivery of an electrically conductive fluid to provide a current flow path between the active and return electrodes is described in commonly assigned U.S. Pat. Nos. 5,697,281 and 6,312,408, the disclosures of which are incorporated by reference herein in their entirety.

In some procedures, it may also be necessary to retrieve or aspirate excess or unwanted materials, e.g., saline, ablation by-products, from the target site. For example, in procedures in the nose, mouth or throat, it may be desirable to aspirate saline so that it does not flow down the patient's throat. In addition, it may be desirable to aspirate resected tissue fragments, blood, mucus, gaseous ablation by-products, etc., from the surgical site. Accordingly, systems of the invention may include an aspiration element or lumen, which may be integral with the device, for aspirating materials from the target site. Furthermore, in some embodiments the device may include one or more aspiration electrode(s) (or digestion electrode(s)) for ablating, or reducing the volume of, resected tissue fragments that are aspirated into the aspiration lumen. Devices incorporating aspiration electrodes are described in commonly assigned U.S. Pat. Nos. 6,238,391 and 6,254,600, the disclosures of which are incorporated by reference herein in their entirety.

FIG. 1 illustrates an electrosurgical system 200 for use with the present invention. System 200 is adapted for performing a procedure on a patient and for estimating a temperature condition at, or adjacent to, a surgical site during the procedure. System 200 includes an exemplary device 201 coupled to a power supply 228.

Device 201 is in the form of a probe or catheter which includes a shaft 202 having a shaft distal end portion 202a, and a shaft proximal end portion 202b attached to a handle 204 which accommodates a connector 206. In this variation the connector 206 is fixed to the shaft 202 via the handle 204. An electrode assembly 210 is operatively disposed at distal end portion 202a. Typically, electrode assembly 210 includes at least one active electrode and at least one return electrode disposed on an electrically insulating electrode support or spacer (e.g., FIGS. 6A–F). Electrode assembly 210 is adapted for applying energy to a target tissue of a patient. Typically, electrode assembly 210 is disposed at the working or distal end of the device. The distal end of probe 201, including electrode assembly 210, may have various configurations, e.g., as described in commonly assigned U.S. Pat. No. 6,296,638, the disclosure of which is incorporated by reference herein in its entirety.

The connector 206 may be within the handle 204 to provide a mechanism for conveniently coupling device 201 to power supply 228, for example, via a connection cable 260. Power supply 228 is adapted for supplying electrical energy to electrode assembly 210. Power supply 228 may comprise, for example, a RF power supply adapted for applying a high frequency alternating-current voltage (ac voltage) to electrode assembly 210.

In an alternative variation of the invention, a connector 206 may be fixedly attached to a cable 260 (e.g., an integrated cable/connector). In such a case, the cable 260 may have a distal end that is fixed to the connector 206, handle 204, and/or shaft 202. A proximal end of the cable 260 will be adapted to engage the power-supply 228 either fixedly or removably.

Device 201 may further include a fluid delivery unit (not shown) adapted for delivering a fluid, such as an electrically conductive liquid (e.g., saline), to electrode assembly 110 and/or to a target tissue during a procedure. Device 201 may further include an aspiration unit (not shown) adapted for aspirating excess or unwanted materials, e.g., excess fluid, resected tissue fragments, and gaseous ablation by-products, from the surgical site during a procedure. The fluid delivery and aspiration units may each take various forms, typically including a proximal tube coupled to a lumen running internal or external to shaft 202, and a distal port (for example, a fluid delivery port or an aspiration port (e.g., FIGS. 4A–B)).

The inventive probe 201 further includes one or more visual temperature-indicating elements 250. Typically, temperature-indicating element 250 is disposed at a location, e.g., exposed on an external surface of shaft distal end portion 202a, where it can be easily viewed by an operator of probe 201, e.g., by viewing element 250 with the naked eye, or via a fiber optic light source and camera (e.g., FIG. 13).

Figure 2A:
FIG. 2A illustrates an electrosurgical probe having a temperature-indicating element according to another embodiment of the invention.
Figure 2B:
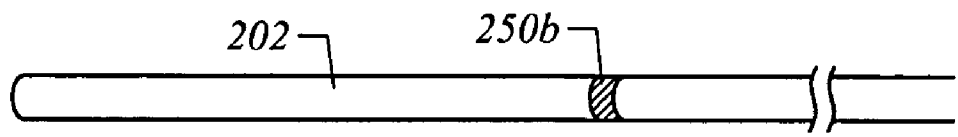
FIG. 2B illustrates an electrosurgical probe having a temperature-indicating element according to another embodiment of the invention.
Figure 2C:
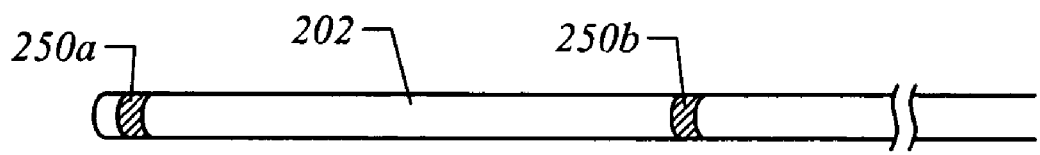
FIG. 2C illustrates an electrosurgical probe having a temperature-indicating element according to another embodiment of the invention.

Often, temperature-indicating element 250 is disposed at the distal end portion of shaft 202, e.g., on, adjacent to, superior to (above), or proximal to electrode assembly 210 (e.g., FIGS. 5A–D, 6A–F) but may be disposed at any point along shaft 202 at a location proximal thereto. For illustrative purposes, the return electrode 211 is shown to be proximal to the support matrix 211. However, the return electrode 211 may be located anywhere along the device. In addition, more than one temperature-indicating element may be employed at one or more locations on shaft 202. For example, one or more elements 250a may be positioned at the working distal end of shaft 202 (see FIGS. 2A and 2C) to indicate the temperature of a target tissue being treated, while one or more other elements 250b may be positioned at a location proximally along the shaft 202 (see FIGS. 2B and 2C) to indicate the temperature of the conductive fluid return. In the variation shown in FIG. 2, the temperature-indicating element 250 is placed about a support matrix 212 which retains the electrodes 210.

One variation of the visual temperature-indicating element 250 typically includes a thermochromic layer of a composition or material, such as an organic polymer in the form of a leuco dye or a liquid crystal, which exhibits a pronounced or readily discernible change in appearance upon exposure to a pre-defined temperature or temperature regime (temperature/time combination). The thermochromic composition is adapted or formulated to undergo one or more distinct visual changes (for example, but not limited to a change in color, shade, hues, saturations or contrasts) upon reaching a particular temperature or range of temperatures. Such change(s) in color may include changing from a colored state to a colorless state or visa-versa, from a dark color to a lighter color or visa-versa. In response to this visual change, application of energy via probe 201 can be discontinued, or the energy level can be decreased.

The present invention may incorporate any number of various types and formulations of thermochromic compositions, including paints, inks, plastics, rubbers, labels, self-adhesive strips, crayons, and synthetic films or sheets, are well known in the art (see, for example, *Encyclopedia of Chemical Technology*, Fourth Edition, J. I. Kroschwitz & M. Howe-Grant, Eds., Published by John Wiley & Sons, Inc.) and may be used with the present invention. A broad range of thermochromic paints are commercially available, e.g., from Lakfabriek Korthals BV, Postbus 135, 1970 AC IJmuiden, The Netherlands and from TMC, Northbrook, Ill. Thermochromic liquid crystal Mylar sheets are available, for example, from Omega Engineering, Inc., Stamford, Conn. One thermochromic ink suitable for use with the present invention is DynaColor™ epoxy screen ink distributed by Chromatic Technologies, Incorporated. This ink is colored below a specific temperature and changes to colorless or to another, lighter color as it is heated through a defined temperature range. This color change is reversible in that the original color is restored upon cooling of the ink.

It may be desirable to place provide some type of protective covering for the temperature element. For example, the thermochromic materials for use with the present invention may be applied to an external surface of a device and then covered by a biocompatible sheath, e.g., comprising a transparent or translucent plastic. Such a sheath may be electrically and/or thermally insulating. In the latter case, the activation temperature of temperature element may be affected by the insulation. However, simple experimentation allows for proper selection of the temperature range of the element and notice as to what external temperature event affects the element.

The temperature element may be formulated with other materials to modify or enhance their color change characteristics. For example, a thermochromic composition may be encapsulated within microscopic capsules or microcapsules, e.g., having diameters in the range of from about 1 µm to 10 µm, and added to a host medium (e.g., a polymer or pigmented resin) to provide a thermochromic composition.

The temperature above which the temperature element begins to change visual appearance shall be referred to as the initial activation temperature of an activation temperature range. The temperature at which the temperature element completes the visual transformation shall define the upper limit of the activation temperature range. The activation temperature range of the temperature element is often a function of the chemical structure or physical configuration of the element or composition forming the element. The thermochromic activation temperature range can be tailored by chemical modification of components of the composition, and/or by adjusting the proportions of one or more components of the composition. The activation temperature range is variable and may be optimized according to the particular type of tissue being treated, e.g., bone, skin, cartilage, and the intended effect on the tissue, e.g., ablation, contraction. For example, a first device intended for ablating hard connective tissue during an arthroscopic procedure may be provided with a first temperature indicating element adapted to indicate a first pre-defined temperature; whereas a second device intended for shrinking collagen containing tissue during a cosmetic procedure may be provided with a second temperature indicating element adapted to indicate a second pre-defined temperature. Typically, the temperatures to be monitored during electrosurgical procedures are well within this range (e.g., from about 40° C. to 95° C.). As one example only, and not to limit the invention in any way, the temperature-indicating element may comprise a material that undergoes a distinct, readily recognized color change when it experiences a temperature increase to 65° C.

The temperature-indicating element may be selected to have more than one specific activation temperatures or temperature ranges. Some thermochromic compositions may undergo a series of color changes with change in temperature, i.e., the temperature-indicating element composition may exhibit a plurality of different colors as the temperature changes, wherein at least one of the different colors is indicative of a particular temperature value or temperature range. For example, the temperature-indicating element may have three activation temperatures, e.g., 45° C., 65° C. and about 80° C., where the element changes colors upon a change from a preferred temperature or range to an acceptable temperature or range to an unacceptable temperature or range, that latter of which may indicate a temperature at which tissue is at a risk of becoming damaged. Thermochromic liquid crystalline materials, e.g., cholesteric liquid crystals, nemetic liquid crystals, and smectic liquid crystals, are highly suitable for such an application. Each thermochromic liquid crystal composition typically exhibits a range of color changes as the temperature changes (increases and decreases) through a defined temperature range. For example, as the temperature increases through a particular temperature range, the composition may change from brown to red, then yellow, green, blue, violet, and black. Liquid crystals may be categorized according to their red start (or "event") temperature and bandwidth (see, for example, the article by D. J. Farino, entitled *Making Surface Temperature Measurements Using Liquid Crystal Thermography* (http://www.electronics-cooling.com/Resources/EC Articles/OCT95/oct95_01.htm)).

In some embodiments, the temperature value indicated by the temperature-indicating element may directly provide a useful estimate of the tissue temperature. In other embodiments, a correction factor may be used to estimate a temperature of the target tissue, based on the temperature value indicated by the temperature-indicating element. The value of such a correction factor may depend, for example, on the location of the temperature-indicating element with respect to the active electrode(s), parameters of the voltage applied to the active electrode(s), and other parameters. As an example only, consider a procedure in which it is desired to heat the target tissue to a temperature of y° C. In a situation where the temperature differential between the temperature indicating element and the target tissue is x° C., the temperature-indicating element can be adapted to show a change in appearance at a temperature of (y–x)° C. Such a change in appearance of the temperature-indicating element may comprise, for example, an alpha-numeric signal, e.g., a text message (see, e.g., FIG. 9C).

Figure 3:
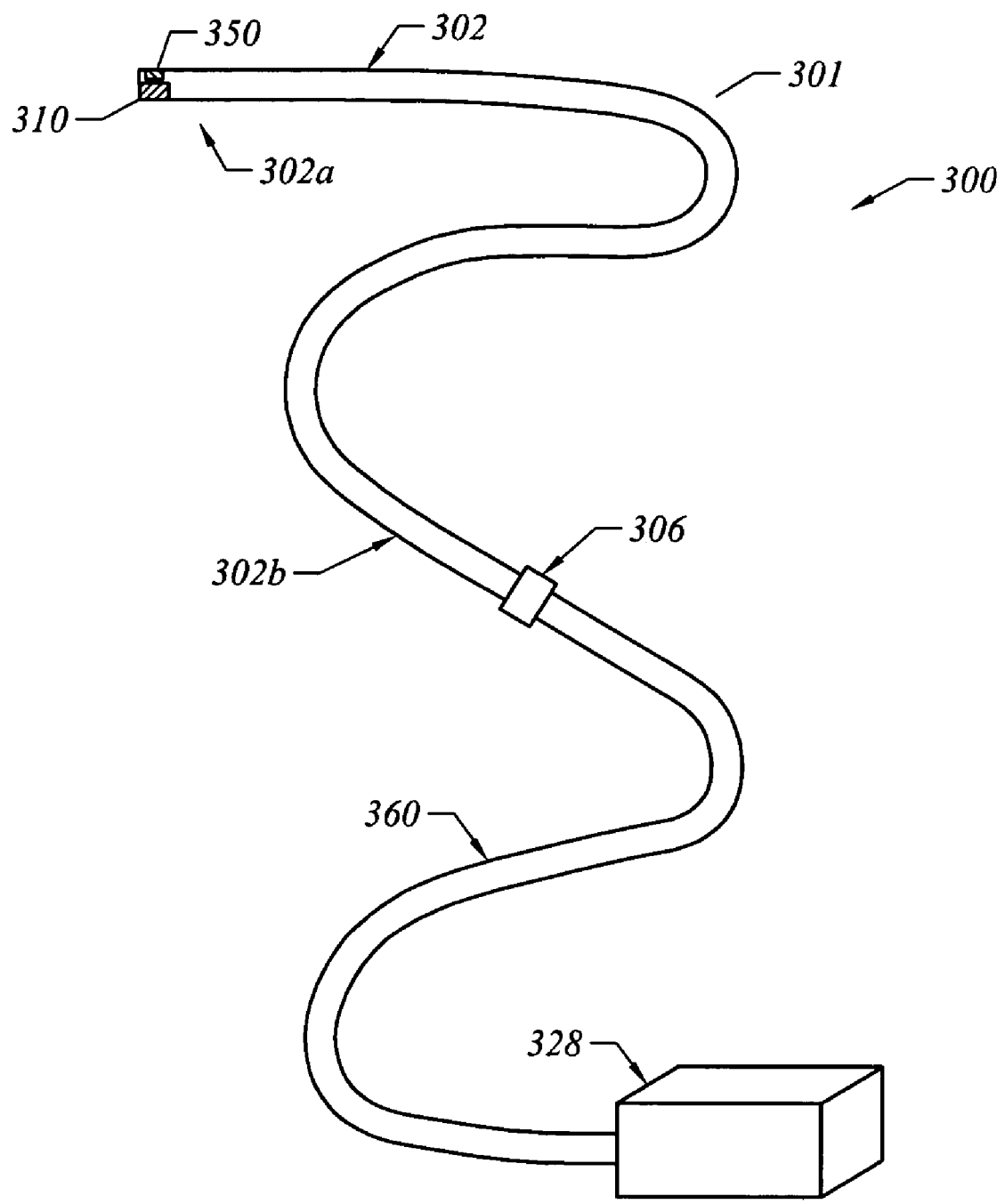
FIG. 3 shows a system incorporating an electrosurgical catheter, the catheter including a temperature-indicating element, according to another embodiment of the invention.

FIG. 3 schematically represents a system 300 including an electrosurgical catheter 301, according to another embodiment of the invention. System 300 has certain features and characteristics similar or analogous to those of electrosurgical apparatus described hereinabove, e.g., with reference to FIG. 1. Catheter 301 includes a shaft having a shaft distal end portion 302*a* and a shaft proximal end portion 302*b*. An electrode assembly 310 and a temperature-indicating element 350 are disposed at shaft distal end portion 302*a*. Electrode assembly 310 is schematically represented in FIG. 3. In practice, assembly 310 may include one or more active electrodes or an active electrode array, and at least one return electrode.

Temperature-indicating element 350 is also represented generically in FIG. 3. Typically, temperature-indicating element 350 comprises a thermochromic composition adapted to undergo at least one thermochromic transition at a pre-defined temperature. The thermochromic transition temperature(s) of temperature-indicating element 350 are usually in the range of from about 40° C. to 95° C. Temperature-indicating element 350 may have various characteristics, elements, and features as described with respect to other embodiments of the invention, e.g., with reference to FIGS. 6A–10. Temperature-indicating element 350 may be used to estimate temperature in the region of electrode assembly 310 and, indirectly, to monitor tissue temperature at a surgical site during an electrosurgical procedure, as is described herein, e.g., with reference to FIG. 2.

System 300 further includes a power supply 328, and a connector cable 360 for coupling catheter 301 to power supply 328. Typically, catheter 301 further includes a connector 306 adapted for receiving connector cable 360 and for coupling electrode assembly 310 to power supply 328. In one embodiment, power supply 328 is adapted to supply RF power to electrode assembly 310. Of course, the invention is not limited to the configuration shown in FIG. 3, but rather, many other configurations are also possible under the invention.

Figure 4A:
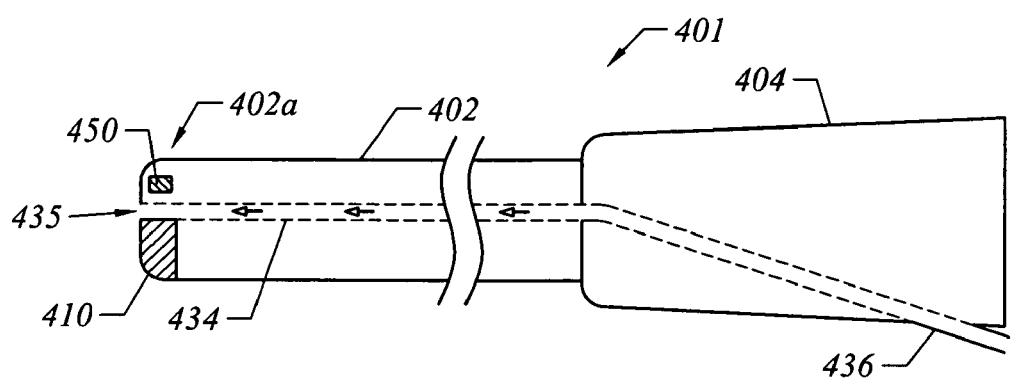
FIG. 4A is a side view of an device having a temperature-indicating element and a fluid delivery element, according to one embodiment of the invention.

FIG. 4A is a side view of an electrosurgical device or probe 401, according to one embodiment of the invention. Probe 401 includes a shaft 402 having a shaft distal end portion 402a and a shaft proximal end portion 402b, and a handle 404. Probe 401 further includes a temperature-indicating element 450 and an electrode assembly 410, both disposed at shaft distal end portion 402a. Both temperature-indicating element 450 and electrode assembly 410 are represented generically in FIG. 4A. Temperature-indicating element 450 and electrode assembly 410 may include various elements and features as described herein with respect to other embodiments of the invention (e.g., with reference to FIGS. 5A–10).

Probe 401 further includes a fluid delivery element comprising a proximal fluid delivery tube 436, a fluid delivery lumen 434, and a distal fluid delivery port 432. The fluid delivery element is adapted for delivering a controlled amount of fluid to the working end of probe 401, or to a target tissue, during a procedure. Fluid delivery tube 436 may be adapted for connection to a suitable fluid source, which may be gravity fed or powered by a pump, as is well known in the art. As shown, lumen 434 lies internal to shaft 402, however, the invention is by no means limited to this configuration.

Figure 4B:
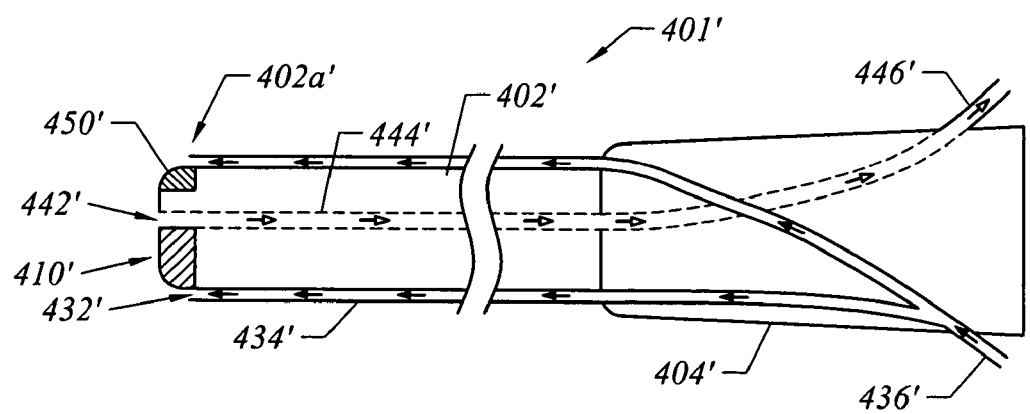
FIG. 4B is a side view of an device having a temperature-indicating element, a fluid delivery element, and an aspiration element, according to another embodiment of the invention.

A fluid delivered to the distal or working end of device 401, or to a target tissue, is represented in FIGS. 4A–B by solid arrows. The fluid delivered by the fluid delivery element may be an electrically conductive fluid (e.g., saline) which completes a current flow path between the active and return electrodes of electrode assembly 410 (e.g., FIGS. 6A–F). Saline delivered by the fluid delivery element may also promote initiation and maintenance of a plasma in the vicinity of the active electrode(s) upon application of a suitable high frequency voltage thereto (e.g., during the Coblation® process, as described hereinabove).

According to one aspect of the invention, a region surrounding the target tissue and the working end of an electrosurgical device may be submersed in a fluid. For example, during certain arthroscopic procedures, a fluid delivered by the device may substantially fill the cavity of a synovial joint. Saline delivered to a target tissue during a procedure may have a NaCl concentration greater than that of isotonic saline. Furthermore, a fluid delivered during a procedure may be a salt solution other than NaCl solution (saline). Various electrically conductive fluids for use in electrosurgery according to the instant invention are described in commonly assigned U.S. Pat. No. 6,149,620, the disclosure of which is incorporated by reference herein in its entirety.

FIG. 4B is a side view of a device or probe 401', according to another embodiment of the invention. Probe 401' includes a number of elements in common with previously described embodiments, e.g., that described with reference to FIG. 4A. Briefly, probe 401' includes a temperature-indicating element 450' and an electrode assembly 410', both disposed at shaft distal end portion 402a'. Probe 401' further includes a fluid delivery element comprising a proximal fluid delivery tube 436', a fluid delivery lumen 434', and a distal fluid delivery port 432'. In the embodiment shown in FIG. 4B, fluid delivery lumen 434' takes the form of an annular gap lying external to shaft 402'. Apparatus having an annular fluid delivery element are described in commonly assigned U.S. Pat. No. 6,066,134, the disclosure of which is incorporated by reference herein in its entirety.

Probe 401' still further includes an aspiration element comprising a proximal aspiration tube 446', an aspiration lumen 444', and a distal aspiration port 442'. The aspiration element is adapted for aspirating excess or unwanted materials, such as, blood, saline, resected tissue fragments, gaseous ablation by-products, etc., from the surgical site during a procedure. Aspiration tube 446' may be adapted for coupling to a suitable vacuum source, as is well known in the art. As shown in FIG. 4B, aspiration lumen 444' lies internal to shaft 402'; however, the invention is by no means limited to this configuration. In some embodiments, the probe may include one or more aspiration electrodes (not shown) adapted for digesting resected tissue fragments, or other debris, drawn into aspiration port 442' via an aspiration stream (represented in FIG. 4B by open arrows). An apparatus having an aspiration element is described in commonly assigned U.S. Pat. No. 6,238,391, the disclosure of which is incorporated by reference herein in its entirety.

Figure 5A:
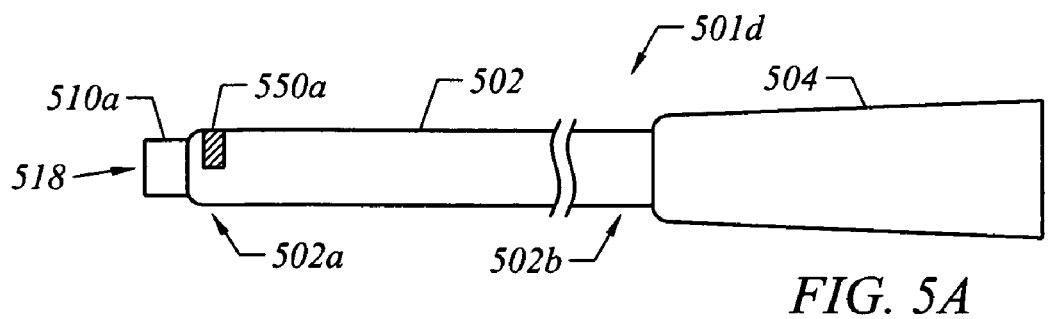
FIGS. 5A–D each schematically represent an electrosurgical device having a temperature-indicating element and an electrode assembly, according to various embodiments of the instant invention.
Figure 5B:
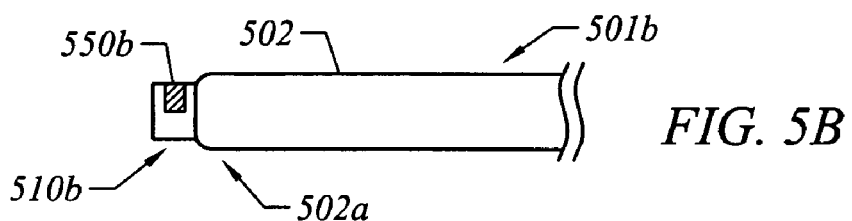
Figure 5C:
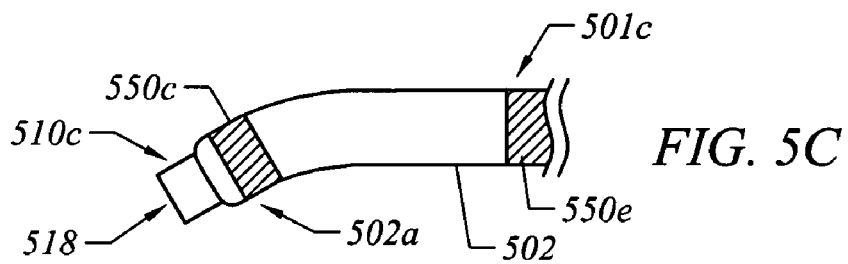
Figure 5D:
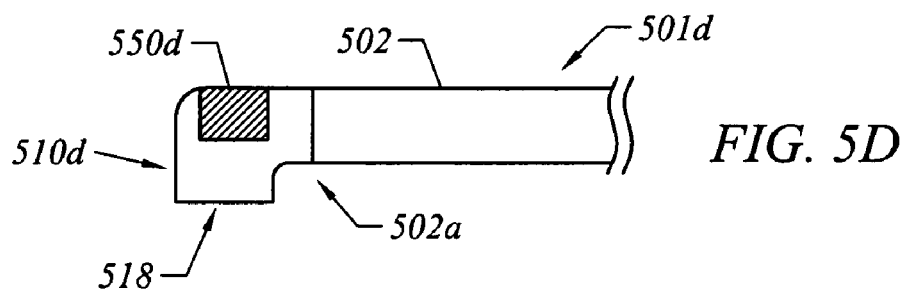

FIGS. 5A–D each schematically represents an electrosurgical device 501a–d, respectively, according to various embodiments of the instant invention. Devices 501a–d have temperature-indicating elements 550a–d and electrode assemblies 510a–d, respectively. Temperature-indicating elements 550a–d and electrode assemblies 510a–d are represented more or less generically in FIGS. 5A–D. Size, dimension, and location of the temperature indicating elements 550a–d shown is only for illustrative purposes. The temperature indicating elements 550a–d may be placed about the shaft 502 of the device or it may be located in discrete places on the device. Furthermore, more than one temperature indicating element 550a–d having either the same activation temperature range or different activation temperature ranges may be used. For example, FIG. 5D illustrates a second temperature-indicating element 550e on a device 501c. In practice, temperature indicating elements 550a–d and electrode assemblies 510a–d may each include various elements or features as described herein with respect to other embodiments of the invention. For example, temperature-indicating elements 550a–d may each comprise: a thermochromic paint applied directly to the device or applied over a primer; an adhesive label, tape, or other printable medium incorporating a thermochromic composition (e.g., a thermochromic ink); a thermochromic synthetic film; an annular band of a rubber or a plastic; or a plurality of thermochromic cells. In the latter case, each cell may have the same or different thermochromic compositions contained therein or applied thereto.

The temperature-indicating elements 550a–d may comprise, for example, a leuco dye, or a liquid crystal having a suitable red start temperature and bandwidth. The liquid crystal may be, for example, a cholesteric liquid crystal.

Thermochromic liquid crystal formulations are available with start temperatures ranging from <−30° C. to >+100° C., and bandwidths ranging from about 0.5° C. to 30° C. The temperature-indicating elements 550a–d may be encapsulated in a plurality of microcapsules. (Microencapsulated thermochromic compositions are commercially available, e.g., from Hallcrest, Inc., Glenview, Ill.) Alternatively, one or more of elements 550a–d may comprise a thermochromic liquid crystal Mylar® sheet or film. A broad range of thermochromic materials may be formulated to undergo a specific color change at pre-defined transition temperatures, as is well known in the art.

In the embodiment of FIG. 5A, device or probe 501a includes a shaft 502 having a shaft distal end portion 502a and a shaft proximal end portion 502b. A handle 504 is attached to shaft proximal end portion 502b. Electrode assembly 510a is disposed axially at the apex or terminus of shaft 502, and temperature indicating element 550a is disposed on shaft distal end portion 502a proximal to electrode assembly 510a. Electrode assembly 510a includes a treatment surface 518 adapted for being positioned with respect to a target tissue during a procedure. For sake of clarity, a return electrode is not illustrated on FIGS. 5A–5D.

With reference to FIG. 5B, probe 501b includes certain elements in common with the embodiment described with reference to FIG. 5A. Only the distal or working end of probes 501b–d are shown in FIGS. 5B–D. Probe 501b has electrode assembly 510b disposed axially at the terminus of shaft 502, and temperature indicating element 550b is disposed on electrode assembly 510b.

FIG. 5C shows probe 501c including shaft 502 having a curved shaft distal end portion 502a. Electrode assembly 510c is disposed at the terminus of shaft 502, and temperature indicating element 550c is disposed proximal to electrode assembly 510c. Other arrangements for an electrode assembly and a temperature-indicating element on a curved shaft are also possible under the invention.

FIG. 5D shows a probe 501d having electrode assembly 510d at shaft distal end portion 502a. Electrode assembly 510d includes treatment surface 518 adapted for opposing or contacting a target tissue during a procedure. As shown in FIG. 5D, treatment surface 518 is arranged laterally on shaft 502. Temperature-indicating element 550d is disposed on electrode assembly 510d at a superior location, where it is readily visible to a surgeon performing a procedure using probe 501d. It is to be understood that the invention is not limited to those configurations shown in FIGS. 5A–D. Furthermore, each of probes 501a–d may include various elements and features as described herein for other embodiments of the invention. For example, one or more of probes 501a–d may include a fluid delivery element, and/or an aspiration element (e.g., FIGS. 1, 4A–B).

Figure 6A:
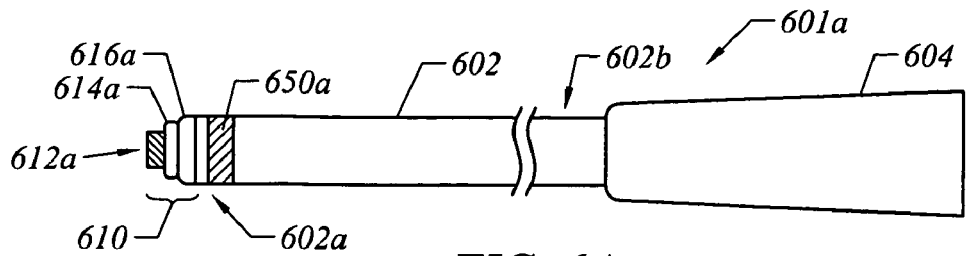
FIGS. 6A–F each schematically represent an electrosurgical device, showing a temperature-indicating element in relation to components of an electrode assembly, according to various embodiments of the instant invention.

FIGS. 6A–E each schematically represents an electrosurgical device 601a–e, respectively, according to various embodiments of the instant invention. Each of FIGS. 6A–E shows a temperature indicating element 650a–e in relation to components of an electrode assembly. With reference to FIG. 6A, probe 601a includes a shaft 602 having a shaft distal end portion 602a and a shaft proximal end portion 602b. A handle 604 is attached to shaft proximal end portion 602b. An electrode assembly 610a is disposed at shaft distal end portion 602a. Electrode assembly 610a includes a distal active electrode or electrode array 612a disposed on an electrically insulating electrode support or spacer 614a, and a return electrode 616a.

Active electrode(s) 612a may have a wide variety of configurations, and each active electrode or electrode terminal may comprise a metal such as stainless steel, molybdenum, platinum, tungsten, palladium, iridium, titanium, or their alloys, and the like. Spacer 614a may comprise, for example, a ceramic, a glass, or a silicone rubber. Return electrode 616a may comprise, for example, an annular band of a metal, such as stainless steel, molybdenum, platinum, tungsten, palladium, iridium, titanium, or their alloys. As an example only, various electrode configurations that may be used in conjunction with the instant invention are described in commonly assigned U.S. Pat. No. 6,296,638, the disclosure of which is incorporated by reference herein in its entirety.

Again with reference to FIG. 6A, probe 601a further includes temperature-indicating element 650a disposed on shaft distal end portion 602a at a location proximal to return electrode 616a. Temperature-indicating element 650a may comprise non-toxic (or low toxicity), FDA-approved, biocompatible materials, or may be encased within such materials. In some embodiments, the temperature-indicating element may be covered by a sheath of biocompatible material (see, e.g., FIG. 7), which may be transparent or translucent. In such instances, the patient's tissue is shielded from direct contact with components of the temperature-indicating element during a procedure.

Figure 6B:
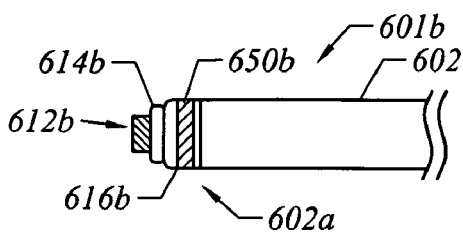

FIGS. 6B–E show, in side view, the working or distal end of probes 601b–e, respectively. Each of probes 601b–e may have features or elements the same, similar, or analogous to those described hereinabove, e.g., with reference to FIG. 6A. With reference to FIG. 6B there is shown probe 601b having a distal active electrode 612b disposed on an electrically insulating electrode support 614b, and a proximal return electrode 616b. Temperature indicating element 650b of probe 601b is disposed on return electrode 616b.

Figure 6C:
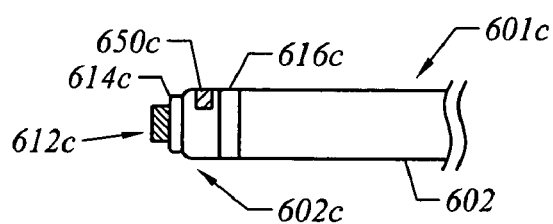

In the embodiment of FIG. 6C, temperature indicating element 650c is disposed distal to return electrode 616c and proximal to spacer 614c. Return electrode 616c is shown as an annular band disposed on shaft distal end portion 602a. However, other configurations for the return electrode are also within the scope of the invention.

Figure 6D:
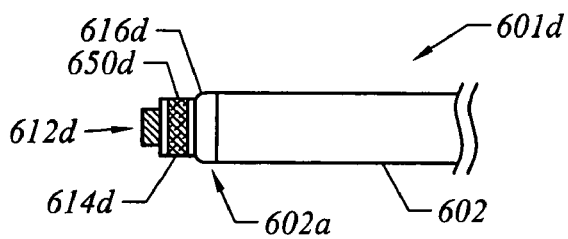

FIG. 6D shows a distal active electrode 612d disposed on an electrically insulating spacer 614d, and a return electrode 616d disposed proximal to spacer 614d. In the embodiment of FIG. 6D, temperature-indicating element 650d is disposed on spacer 614d between active electrode 612d and return electrode 616c.

Figure 6E:
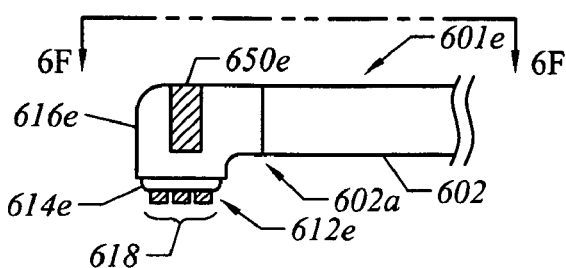
Figure 6F:
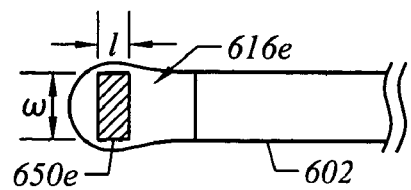

In the embodiment of FIG. 6E, electrically insulating electrode support or spacer 614e is arranged laterally on shaft distal end portion 602a. A plurality of active electrodes 612e, or an array of active electrode terminals, is arranged on spacer 614e. Return electrode 616e is disposed superior to (above) spacer 614e. FIG. 6F is a plan view of the device of FIG. 6E taken along the lines 6F–6F. Temperature-indicating element 650e is disposed at a superior location on return electrode 616e. As shown in FIG. 6F, temperature-indicating element 650e is represented as being substantially rectangular in outline with its long axis arranged substantially orthogonal to the longitudinal axis of probe 601e. However, other configurations for the temperature-indicating element are also within the scope of the invention. Temperature-indicating elements of the invention, e.g., element 650e, typically have a length, $l$ in the range of from about 1 mm to 3 cm, more usually from about 2 mm to 2 cm, and often from about 3 mm to 1 cm; and typically have a width, w in the range of from about 1 mm to 5 cm, more usually from about 2 mm to 3 cm, and often from about 3 mm to 2 cm. Of course, in some embodiments the temperature-indicating element may comprise an annular band which encircles the shaft (see, e.g., FIG. 10).

Each of temperature-indicating elements 650a–e may comprise a suitable thermochromic composition, appropriately selected or formulated to provide a discernible change in appearance (e.g., a color change) in response to a specific temperature condition or temperature regime. In some embodiments, the temperature-indicating element may be affixed directly to various components of the probe or device. Alternatively, an additional component, for example, a temperature indicator base, may be affixed to the probe, and the temperature-indicating element 650a–e may be disposed on the temperature indicator base (see, e.g., FIG. 8).

Shafts 602a–e are shown in FIGS. 6A–E as being essentially linear or straight. However, according to the invention the shaft, and in particular the shaft distal end portion, may be bent or curved at various angles, typically in the range of from about 5° to 90° to the longitudinal axis of the probe. A suitably curved shaft may facilitate access or manipulation of the working end of the device with respect to a target tissue during certain procedures. Devices having curved shafts are described in commonly assigned U.S. Pat. No. 6,296,638, the disclosure of which is incorporated by reference herein in its entirety.

Figure 7:
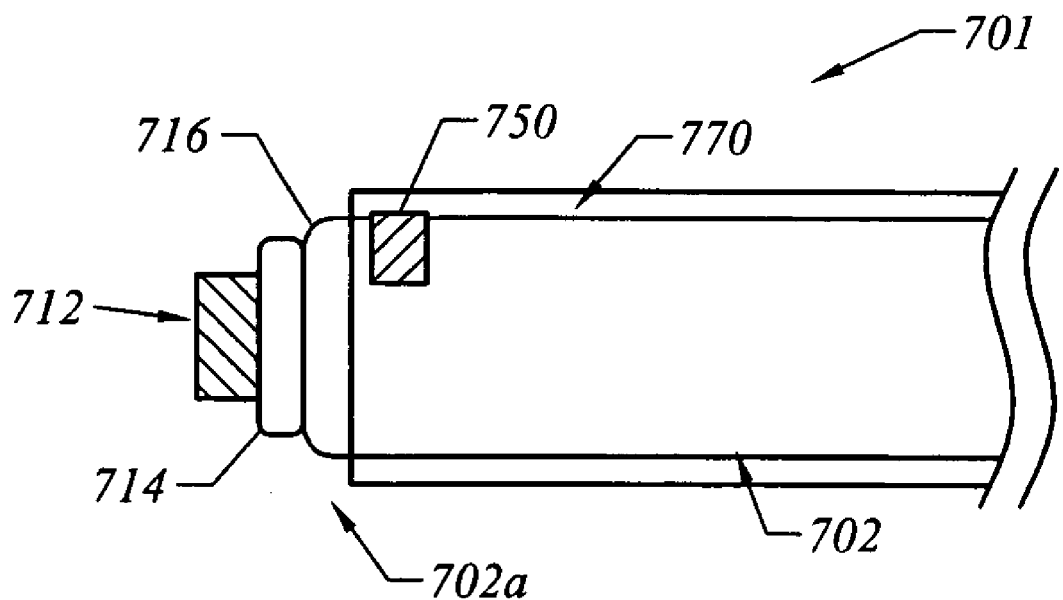
FIG. 7 is a side view schematically representing an electrosurgical device having a temperature-indicating element encased within a sheath, according to another embodiment of the invention.

FIG. 7 is a side view schematically representing an electrosurgical device 701 having a temperature-indicating element encased within a sheath, according to another embodiment of the invention. Only the distal or working end of device 701 is shown in FIG. 7. Device 701 may include various elements or features the same, similar, or analogous to those of other embodiments of the invention, e.g., as described herein with reference to FIGS. 1–10. FIG. 7 shows a distal active electrode 712 disposed on an electrically insulating electrode support 714, and a proximal return electrode 716.

A temperature-indicating element 750 is disposed on shaft distal end portion 702a at a location proximal to return electrode 716. Other configurations for the return electrode and temperature-indicating element are also within the scope of the invention. Temperature-indicating element 750 typically includes a thermochromic composition, such that temperature-indicating element 750 undergoes a readily discernible change in appearance in response to a pre-defined change in temperature, e.g., at one or more thermochromic transition temperatures of the thermochromic composition. For many electrosurgical procedures, the one or more pre-defined temperatures will usually be within the range of from about 40° C. to 95° C.

In the embodiment of FIG. 7, device 701 includes a sheath 770 of biocompatible material lying external to shaft 702. Sheath 770 extends distally to a point whereby temperature-indicating element 750 is at least partially covered by sheath 770. As an example, sheath 770 may comprise a shrink wrap tube. In some embodiments, sheath 770 may completely cover temperature-indicating element 750, such that a patient's tissue is shielded from temperature-indicating element 750, by sheath 770, during a procedure. In one embodiment, sheath 770 is a transparent or translucent layer which allows a user (surgeon) of device 701 to easily view indicating element 750 while operating device 701. Sheath 770 may extend proximally from a location distal of temperature indicating element 750 to the handle of device 701.

Sheath 770 may comprise a polymeric material, such as various plastics. In some embodiments, sheath 770 may comprise an electrically insulating cover over shaft 702, and sheath 770 may terminate at a defined location on shaft distal end portion 702a to define return electrode 716 as an exposed portion of shaft 702. It is to be understood that the invention is by no means limited to the electrode configuration shown in FIG. 7.

According to another embodiment, sheath 770 may comprise a transparent or translucent colored material having a first color (e.g., blue), while indicating element 750 may be colored (e.g., yellow) at body temperature and may become colorless and translucent at an elevated temperature, such that the appearance of element 750, as seen through sheath 770, changes in color (e.g., from green to blue) at the elevated temperature. As an example, certain thermochromic compositions are known to exhibit a thermochromic transition from opaque and colored to colorless and translucent with changing temperature.

In another embodiment, sheath 770 may itself comprise a thermochromic material which either allows visualization, or changes the appearance, of an underlying element, only under certain pre-defined temperature conditions. For example, sheath 770 may comprise a thermochromic composition that changes from opaque to transparent at a pre-defined temperature to reveal one or more alpha-numeric characters lying below sheath 770.

Figure 8:
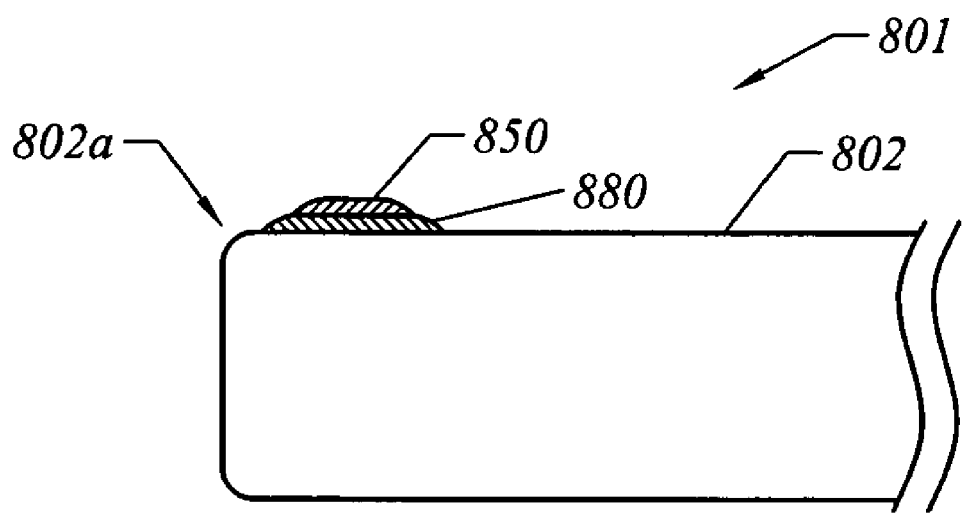
FIG. 8 is a partial longitudinal sectional view of a distal portion of an electrosurgical device having a temperature-indicating element disposed on a temperature indicator base element, according to one embodiment of the invention.

FIG. 8 is a partial longitudinal sectional view of a distal or working end of an electrosurgical device 801, according to one embodiment of the invention. Device 801 includes a shaft 802 having a shaft distal end portion 802a. Device 801 typically includes certain elements or features that are at least somewhat analogous to those described for other embodiments of the invention, e.g., with reference to FIGS. 2–3, 6A–F. Thus, device 801 will typically include an electrode assembly disposed at shaft distal end portion 802a. (The electrode assembly is omitted from FIG. 8 for the sake of clarity.)

Device 801 further includes a temperature indicator base or pad 880 disposed on shaft distal end portion 802a. Device 801 still further includes a temperature indicating element 850 disposed on indicator base 880. Indicator base 880 may serve a range of different functions, and may comprise various materials or compositions. The composition of indicator base 880 is typically dependent, at least in part, on the intended function of base 880. According to one embodiment, base 880 may comprise a thermally insulating or thermally reflective material, wherein base 880 serves to thermally insulate or isolate temperature indicating element 850 from shaft 802. According to one embodiment, base 880 may comprise an electrically insulating material which serves to electrically insulate element 850 from other components of device 801.

In another embodiment of the invention, indicator base 880 may comprise a material adapted to affix, or adhere, element 850 to shaft 802. For example, in embodiments where element 850 comprises a thermochromic paint, base 880 may comprise a primer layer to which the thermochromic paint is applied. In another example, temperature-indicating element 850 may comprise a printable medium printed with thermochromic ink, and base 880 may comprise an adhesive for affixing the printable medium to shaft 802. In another embodiment, base 880 may be adapted to maximize or promote the appearance of element 850 before and/or after a thermochromic transition (change in color). For example, base 880 may be variously colored (e.g., black or white, depending on the color change(s) of the thermochromic material) to enhance visualization of the thermochromic transition of element 850. In other embodiments, indicator base 880 may be omitted, and a thermochromic paint or varnish, a printable medium, or a thermochromic film may be applied directly to shaft 802, with or without a covering element (e.g., a light-transmitting sheath, FIG. 7). Media printable with thermochromic ink include synthetic films, glass, ceramics, thermoplastics, and various fabrics. Thermochromic inks and thermochromic paints are commercially available, e.g., from Matsui International Co., Inc., Gardena, Calif.

FIGS. 9A–C each schematically represent an electrosurgical device having a temperature indicating element disposed on a distal end portion of a shaft of the device, according to three different embodiments of the instant invention. FIG. 9A shows a distal end portion 902a of a shaft 902 of a device, as seen in plan view (e.g., FIG. 6F). The device includes a temperature-indicating element 950 disposed at shaft distal end portion 902a. Indicating element 950 comprises a plurality of thermochromic cells 954a–n. Five such thermochromic cells are shown in FIG. 9A, although other numbers are also within the scope of the invention.

In one embodiment, each of the plurality of thermochromic cells 954a–n comprises a different thermochromic composition, such that each cell 954a–n has different, defined thermochromic properties. For example, each cell 954a–n may have a different thermochromic transition temperature. Thus, the plurality of cells 954a–n may undergo a color change at a corresponding plurality of different temperatures. In some embodiments, indicating element 950 may be configured such that cells 954a–n sequentially undergo a thermochromic transition, e.g., from left to right, as the temperature at shaft distal end portion 902a increases within a defined temperature range. For example, cells 954a, 954b, 954c, and 954d may successively undergo a thermochromic transition at temperatures of 50° C., 55° C., 60° C., and 65° C., respectively. The type of color change, e.g., from a first color to a second color, or from a colored to a colorless state, may be the same or different for cells 954a–n.

Indicating element 950 may be arranged circumferentially on shaft distal end portion 902a, and indicating element 950 may conform to the external surface of shaft 902. Typically, the device of FIG. 9A will include an electrode assembly having at least one active electrode. Electrode(s) are omitted from FIG. 9A for the sake of clarity.

FIG. 9B is a plan view of the distal or working end of an device, showing a temperature indicating element 950' disposed at shaft distal end portion 902a. Temperature-indicating element 950' is configured to display one or more of a plurality of numeric values according to a defined temperature condition of shaft distal end portion 902a. As shown, a plurality of numeric values is indistinctly visible, while one numeric value is distinctly displayed to indicate a temperature corresponding to the displayed numeric value (i.e., 55° C.). In alternative embodiments, all numeric values other than that indicative of the actual temperature condition may be invisible. As an example, numeric values corresponding to a range of temperatures, or other alpha-numeric characters, may be made to sequentially appear at particular thermochromic transition temperatures by formulating a plurality of thermochromic compositions to undergo a color change at those temperatures corresponding to each of the plurality of numeric values.

In one embodiment, indicating element 950' may comprise a plurality of thermochromic cells (see, e.g., FIG. 9A). Each thermochromic cell may have a different thermochromic formulation, such that each cell has a different thermochromic signature or thermochromic transition characteristics. As an example, each of the plurality of thermochromic cells may be adapted to display a different numeral, and the plurality of thermochromic cells can be formulated to undergo a thermochromic transition, e.g., from colored to colorless, at the temperature corresponding to the numeral(s) which it displays. Thus, when the thermochromic composition becomes colorless, the numeral underlying the thermochromic composition becomes readily visible to an operator of the device, thereby indicating the temperature corresponding to the numeric value. In alternative embodiments, alpha-numeric characters may be used to signify a particular temperature or temperature range, as opposed to showing actual temperature values. For example, the numerals I–V (or the letters A–E) could be used to signify five different temperatures or temperature ranges, e.g., numerals I, II, and III could correspond to 45° C., 50° C., and 55° C., respectively.

FIG. 9C also shows a plan view of the distal or working end of an device, the device including a temperature indicating element 950" disposed at shaft distal end portion 902a. Temperature indicating element 950" includes a message unit 956 and is adapted to display one or more alpha-numeric characters, or a message, when a defined temperature condition applies. For example, according to one embodiment a message may be imprinted on message unit 956 in a thermochromic material (e.g., a thermochromic ink or thermochromic paint), wherein the thermochromic material is formulated to undergo a color change (e.g., from brown to green) at a pre-defined temperature. Alternatively, a text message imprinted on an underlying medium may be overlaid with a layer of thermochromic material formulated to undergo a thermochromic transition from colored/opaque to colorless/translucent at a defined temperature, whereby the underlying text message becomes visible through the thermochromic layer at the defined temperature.

In one embodiment, a message displayed by indicating element 950" may be a text message, e.g., for warning an operator of the device that sufficient heat had been generated at the working end of the device for treatment of the tissue. To cite just a few examples, following a thermochromic transition, element 950" may be adapted to display one or more of the following messages "REDUCE POWER," "REMOVE PROBE," or "END!". As an example of how element 950" may be useful in practice, consider a procedure for electrosurgically shrinking collagen containing tissue (for which a temperature in the range of 60° C. to 70° C. may be desired). Element 950" may be adapted, formulated, and configured to reveal one or more text messages, e.g., when exposed to a temperature below 60° C., and/or in excess of 65° C. Apparatus and procedures for shrinking collagen-containing tissue are described in commonly assigned U.S. Pat. Nos. 6,309,387 and 6,277,112, the disclosures of which are incorporated by reference herein in their entirety.

Figure 10:
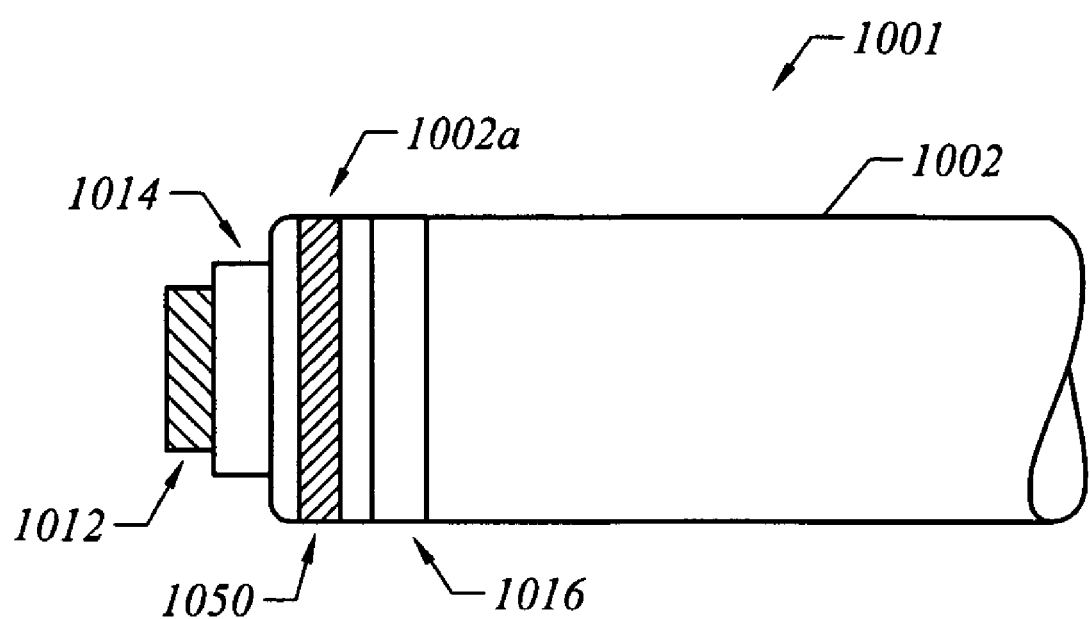
FIG. 10 is a side view schematically representing a shaft distal end portion of an electrosurgical device having an annular temperature-indicating element, according to another embodiment of the invention.

FIG. 10 is a side view schematically representing a distal or working end of an electrosurgical device 1001, according to another embodiment the invention. Device 1001 includes a shaft 1002 having a shaft distal end portion 1002a. Device 1001 further includes an electrically insulating electrode support or spacer 1014, at least one active electrode 1012 disposed on support 1014, and a return electrode 1016 spaced proximally from active electrode 1012.

Device 1001 still further includes a temperature-indicating element 1050 on shaft distal end portion 1002a. Temperature-indicating element 1050 is in the form of a thermochromic annular band, which may comprise, for example, a plastic or a rubber having a thermochromic composition incorporated therein. The annular band and the thermochromic composition may be formulated and configured to undergo a distinct change in appearance, due to a thermochromic transition, upon exposure to a pre-selected temperature.

Temperature-indicating element 1050 may be encased within a sheath (e.g., FIG. 7) and/or may be disposed on a temperature indicator base (e.g., FIG. 8). Furthermore, temperature indicating element 1050 may be delineated or divided into a plurality of distinct thermochromic cells (e.g., FIG. 9A), and may be adapted to display one or more alpha-numeric characters in response to a defined temperature (e.g., FIGS. 9B–C). Although element 1050 is shown in FIG. 10 as being located distal to return electrode 1016 and proximal to spacer 1014, other configurations are also within the scope of the invention (see, e.g., FIGS. 6A–F).

FIGS. 11A–C schematically represent use of a device in a surgical procedure during which a temperature indicating element of the device undergoes a visual change. FIG. 11A schematically represents an electrosurgical device or probe 1101 including a shaft 1102 having a shaft distal end portion 1102a. Shaft distal end portion 1102a is positioned with respect to a target tissue, TT to be treated. Probe 1101 further includes a temperature indicating element 1150 disposed at shaft distal end portion 1102a. Temperature indicating element 1150 typically includes a thermochromic material, and is adapted to undergo a readily discernible change in appearance in order to indicate a temperature condition to a user of probe 1101. Typically, element 1150 is configured to be readily visible to the surgeon during use of probe 1101, e.g., when viewed from a location indicated by the eye, EY of the surgeon.

Temperature indicating element 1150 may include various elements, features, and characteristics as described hereinabove for temperature indicating elements according to various embodiments of the invention (e.g., with reference to FIGS. 6A–10). Similarly, probe 1101 may include various elements, features, and characteristics as described hereinabove for various devices according to other embodiments of the invention (e.g., with reference to FIGS. 1–10). Thus, probe 1101 typically includes at least one active electrode or electrode terminal adapted for applying energy to the target tissue to be treated. Electrodes are omitted from FIGS. 11A–C for the sake of clarity.

Probe 1101 is coupled to an electrosurgical generator or power supply 1128 via a cable 1160. Typically, power supply 1128 is adapted for supplying a RF, alternating-current voltage (ac voltage) to the target tissue via probe 1101. During application of energy to the target tissue, shaft distal end portion 1102a is positioned adjacent to, or in contact with, the target tissue. As shown, a remote control unit or switch 1190 may be coupled to power supply 1128. As an example, unit 1190 may comprise one or more foot pedals for controlling power output from power supply 1128. An electrosurgical apparatus having foot pedal controls is described fully in commonly assigned U.S. Pat. No. 6,264,650 (Atty. Ref. No. S-5), the disclosure of which is incorporated by reference herein in its entirety.

FIGS. 11B and 11C show enlarged views of the distal end of probe 1101 at time $T_1$ and time $T_2$, respectively. Time $T_1$ represents a stage in the procedure before the working end of probe 1101 has been heated to a an initial activation temperature for the respective temperature indicating element 1150. It can be observed that at time $T_1$ element 1150 has a first appearance. As an example only, element 1150 may comprise a liquid crystal exhibiting a brown color at time $T_1$.

With reference to FIG. 11C, time $T_2$ represents a stage where the working end of probe 1101 has attained a particular pre-defined temperature, as indicated by element 1150 adopting a second appearance, wherein the second appearance is readily discernible from the first appearance. For example, the second appearance may signify that a desired target temperature for the procedure has been attained. As an example, the second appearance may be a green color indicative of a temperature in the middle of the thermochromic liquid crystal bandwidth. Thus, the change in appearance of element 1150 at time $T_2$ may signal the surgeon that the application of energy to the target tissue may be discontinued, and the procedure can be brought to a satisfactory conclusion. Such changes in appearance of element 1150 in response to change in temperature may be obtained by suitable formulation of a thermochromic composition as a component of element 1150, as described hereinabove.

According to an alternative aspect of the invention, a change in appearance of element 1150 at time $T_2$ may inform the surgeon of the heat adjacent to the procedure and to adjust the level of power supplied to device 1101 from power supply 1128. It should be noted that the temperature indicating element may give a dynamic visual indication of temperature at a location adjacent to the device. Once the surgeon stops treatment or the site cools, the temperature indicating element will revert to its natural state (e.g., a clear color.)

Figure 12:
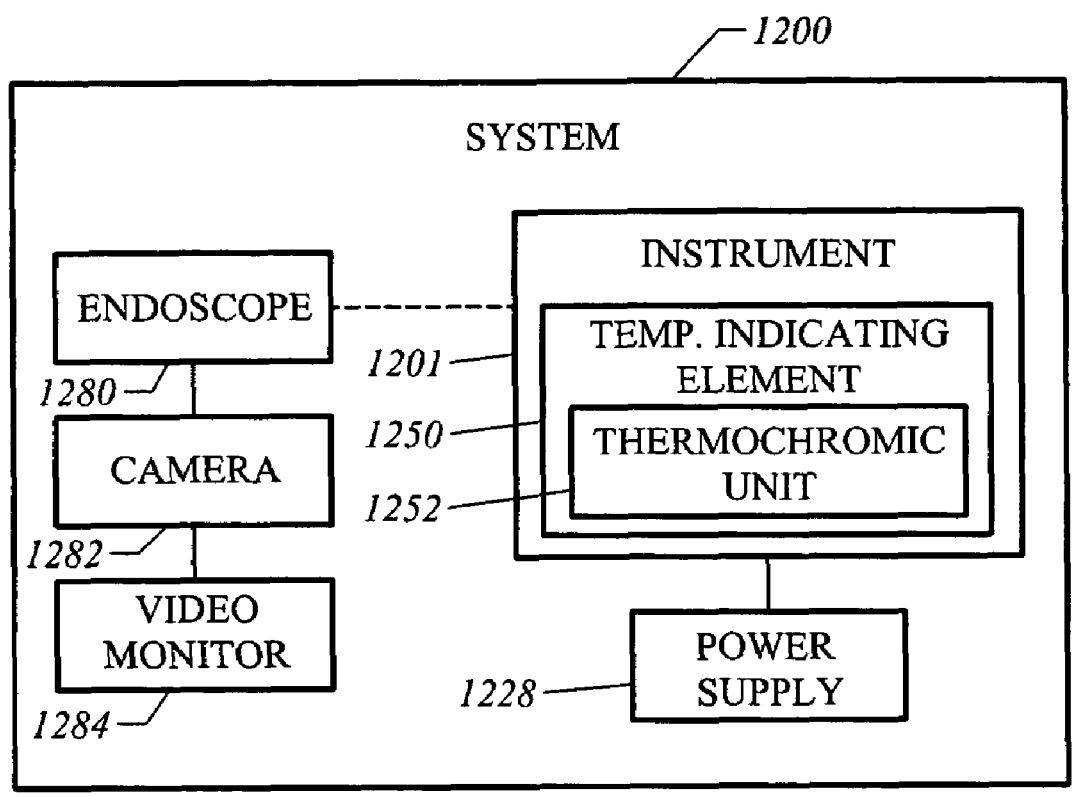
FIG. 12 is a block diagram schematically representing an endoscopic electrosurgical system, according to another embodiment of the invention.

FIG. 12 is a block diagram schematically representing an endoscopic electrosurgical system 1200, according to another embodiment of the invention. System 1200 typically includes an endoscope 1280; an device 1201, which may be adapted for use in conjunction with endoscope 1280; a power supply 1228 for supplying power to device 1201; as well as a camera 1282 and a monitor 1284 adapted for viewing a working end of device 1201 and the surgical site. Device 1201 typically comprises an electrosurgical catheter or an electrosurgical probe having an electrode assembly disposed at the working end of the device (e.g., as described hereinabove). The electrode assembly is adapted to apply electrical energy to a target tissue during a procedure.

Device 1201 is adapted for providing a visual indication to the surgeon, via camera 1282 and monitor 1284, of a temperature condition of the working end of the device. Accordingly, device 1201 includes a temperature-indicating element 1250 adapted to undergo a change in appearance in response to one or more pre-defined temperature conditions. As shown, temperature-indicating element 1250 includes a thermochromic unit 1252 having a thermochromic composition incorporated therein. Thermochromic compositions are well known in the art, and can be tailored or formulated, e.g., by chemical modification, such that one or more thermochromic transitions of the composition occur at defined temperature values. Typically, temperature-indicating element 1250 is disposed at the distal or working end of device 1201, at a location that is readily visualized by the surgeon via camera 1282 and monitor 1284. By observing the working end of device 1201, the surgeon can monitor a temperature condition adjacent to the target tissue. For example, power supplied from power supply 1228 to device 1201 can be adjusted according to the appearance of temperature indicating element 1250. Alternatively, if element 1250 indicates that a desired target temperature for the procedure has been achieved, treatment may be discontinued, thereby reducing the risk of thermal damage to underlying or adjacent, non-target tissue.

Figure 13:
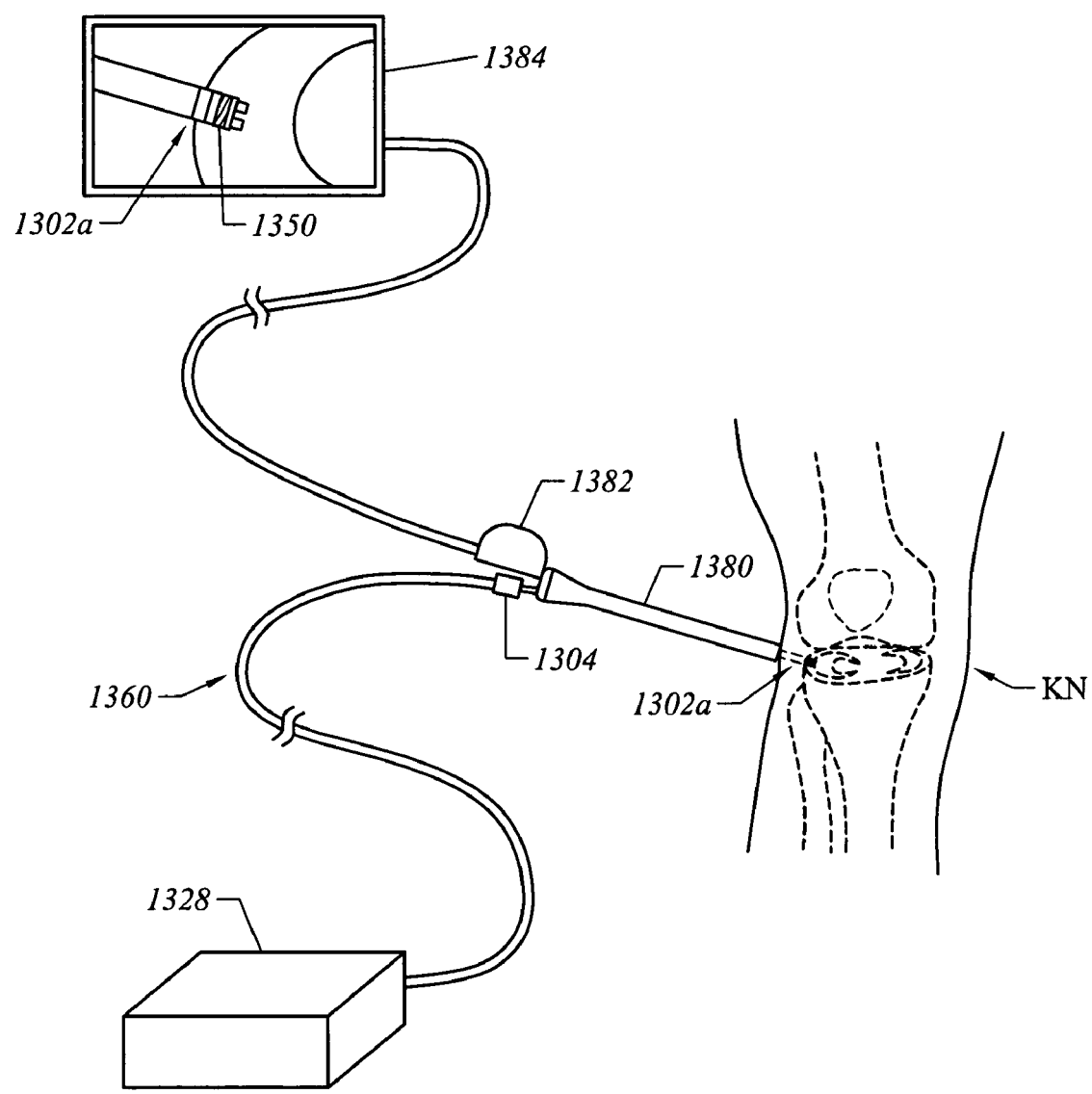
FIG. 13 schematically represents an arthroscopic procedure performed using a device having a temperature-indicating element, according to another embodiment of the invention.

FIG. 13 schematically represents an arthroscopic procedure being performed on a patient's knee joint, KN using an electrosurgical system 1300, according to another embodiment of the invention. System 1300 includes an arthroscope 1380, a camera 1382, and a monitor 1384. A device (largely concealed by arthroscope 1380 in FIG. 13) includes a shaft distal end portion 1302a located at the working end of the device. Typically, the device includes an electrode assembly disposed at shaft distal end portion 1302a, wherein the electrode assembly includes at least one active electrode, disposed on an electrically insulating spacer, and a return electrode. (The electrode assembly is not shown in FIG. 13 for the sake of clarity.) The device is coupled to a power supply 1328 via a connector cable 1360. Power supply 1328 is adapted for applying a high frequency voltage to the electrode assembly.

Again with reference to FIG. 13, temperature-indicating element 1350 is disposed at shaft distal end portion 1302a. Typically, element 1350 comprises a thermochromic composition, and is adapted to provide a visual indication to the surgeon of one or more temperature conditions at the working end of the device by undergoing at least one pre-defined thermochromic transition. The visual indication provided to the surgeon may indicate the progress (e.g., completion) of a procedure, and reduces the risk of an excessively high temperature condition at the surgical site. Accordingly, thermal damage to adjacent or underlying, non-target tissue may be avoided. For greater clarity, temperature-indicating element 1350 is depicted on the monitor image of FIG. 13. Temperature-indicating element 1350 may include various elements, features, and characteristics of temperature indicating elements described herein with reference to other embodiments of the invention.

In an alternative embodiment, an electrosurgical device may be introduced to a joint cavity or other target site (e.g., percutaneously), and an arthroscope (or other endoscope) may be separately introduced to the surgical site to allow visualization of the target site and the temperature indicating element via a video monitor.

Although FIG. 13 shows a procedure on a knee joint, the invention is also applicable to a broad range of open and endoscopic procedures on various tissues and organs, as described hereinabove.

Figure 14:
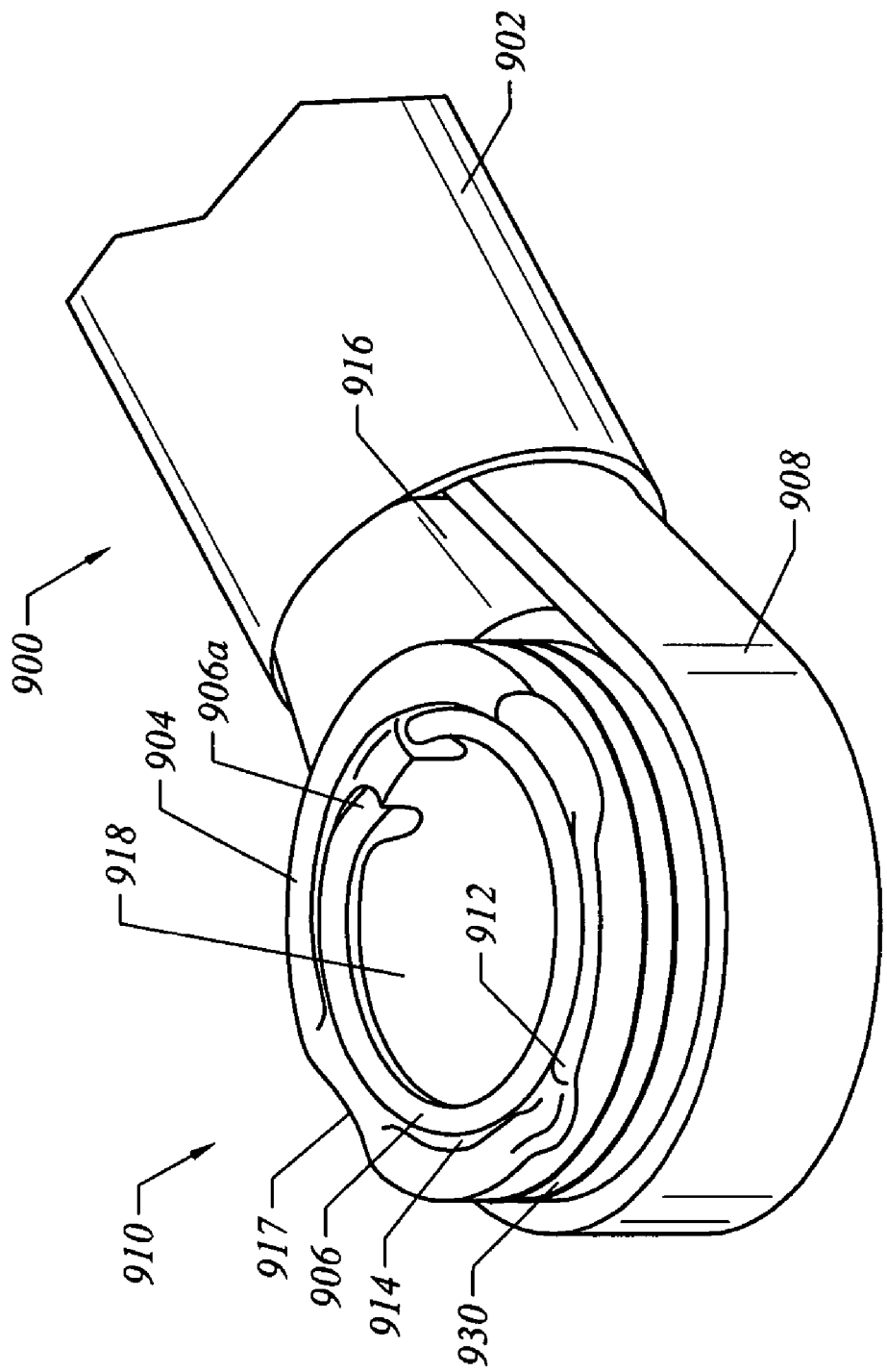
FIG. 14 illustrates an electrosurgical probe having a temperature-indicating element positioned on an electrode support.

FIG. 14 illustrates a perspective view of a tissue treatment member or head 910 of another probe 900 having a temperature indicator 930. Tissue treatment member 910 has a generally annular or loop configuration.

Tissue treatment member 910 includes an electrode support 904 extending from and connected to the distal end of shaft 902 of probe 900. Additionally, a base 916 may separate and further affix the support 904 to shaft 902. Support 904 supports an active electrode 906 and a return electrode 908 in a spaced apart relationship. The support may be made of an electrically non-conducting material such as, for example, ceramic or a plastic. In the illustrated embodiment, active electrode 906 has ends 906a extending into and through openings in support structure 904 to a power supply via one or more conducting members (not shown). Return electrode 908 is operatively connected to the power supply via one or more conducting members (not shown).

Support 904 has an annular or circular configuration and a cavity or recess 914 within a tissue contacting surface 912 for holding active electrode 906. Preferably, active electrode 906 has a shape and configuration that allows it to cooperatively fit within recess 914. While the illustrated embodiment provides a support 904 and active electrode 906 as an annular, loop, ring or circular configuration, their respective shapes and that of recess 914 may vary widely, e.g., serpentine, rectangular, oblong, etc. Additionally, more than one cavity may be provided in the support wherein each cavity may support one or more electrodes. Active electrode 906 may be spaced a predetermined distance from the target tissue by properly pre-selecting the depth of the cavity 914 and the size, diameter or thickness of the electrode. Preferably, active electrode 906 is positioned such that a portion of its surface is flush with or just below the tissue-contacting surface 912 of support 904. In the particular variation illustrated, cavity 914 is provided at a depth on the inside top surface of support 904 and active electrode 906 has a diameter and a thickness such that, when active electrode 906 is operatively provided within cavity 914, tissue contacting surface 912 is substantially flush and smooth (or, as stated above, the active electrode may be positioned below or recessed within cavity 914). In addition to operative advantages, such a configuration serves to protect active electrode 906 from damage during surgery. Other variations are contemplated, for example, where cavity 914 and thus active electrode 906 seated therein are provided at a depth on the outer, top surface of support 904 or on a lateral or perimeter surface of support 904.

As shown the probe 900 may also include a temperature indicator 930. Temperature indicator 930 may be as described above. It may have a band shape that extends circumferentially about the support 904. The band may be positioned within an annular gap such that the temperature indicator is flush with the electrode support tissue treatment surface. The temperature indicator may be divided into one or more discrete components or it may be continuous as shown.

Return electrode 908 is provided about the perimeter, circumference or outer surface of support 904 such that support 904 is partially positioned or extends between active electrode 906 and return electrode 908. Similarly, return electrode 908 has a shape and configuration that allows it to fit about support 904. Such a support and electrode configuration provides structural robustness to both electrodes. While return electrode 906 has a clip or loop configuration in the illustrated embodiment, it may have any suitable configuration and position with respect to support 904 and active electrode 906. As shown return electrode 906 surrounds the body of the support 904 such that it is concentric with support 904 and active electrode 906, but has a width or height dimension which is less than that of support 904 such that return electrode 906 does not cover either the active (upper) or inactive (lower) portions of support 904. Accordingly, when treating tissue in a narrow space such that both the active and inactive sides of support 904 contact tissue, tissue at only the active side is ablated because the plasma generated as a result of the application of high frequency voltage via active electrode 906 does not extend to the lower side of support 904.

Electrodes 906 and 908 may be made of any of the electrode materials previously mentioned. Preferably, active electrode 906 is made of a material of that which undergoes minimal oxidation and has a low electrical resistivity, e.g., tungsten or tantalum. Such materials result in an ablated tissue surface that is minimally discolored and has minimal thermal damage. Examples of materials which may be used for return electrode 908 are stainless steel, copper and alloys thereof. Optional additional features of support 904 include one or more cut-out or recessed regions 917 and one or more openings or apertures 918. More particularly, the tissue-contacting surface 912 is recessed in one or more locations 917 to facilitate fluid flow within cavity 914 and contact with active electrode 906. While the illustrated embodiment provides recessed regions 917 about the circumference of annular active electrode 906 that extend the thickness of support 904, such recessed regions may be located internally to the electrode's annulus or within the boundary of the electrode loop. Aperture 918 further facilitates fluid circulation about active electrode 906 to increase conductivity in the contacted tissue area. Additionally, opening 918 acts as a vent to prevent heat from accumulating adjacent to the tissue treatment surface as well as allows air or gas bubbles that are formed during ablation to escape from the tissue treatment zone. While only a single opening 918 positioned concentrically within the electrode loop is illustrated, multiple openings may be provided in any suitable pattern within the space defined by active electrode 906 or outside the perimeter or both.

While the exemplary embodiments of the present invention have been described in detail, by way of example and for clarity of understanding, a variety of changes, adaptations, and modifications will be apparent to those of skill in the art. In addition, it is to be understood that certain elements or features of various disclosed embodiments may be substituted for corresponding or analogous elements or features of other disclosed embodiments, or may be combined with elements and features of other disclosed embodiments, without departing from the scope of the instant invention. Therefore, the scope of the present invention is limited solely by the appended claims.

What is claimed is:

1. An electrosurgical device for use with a power supply, comprising:
    a shaft having a shaft distal end portion and a shaft proximal end portion;
    an electrode assembly comprising at least one active electrode disposed near the shaft distal end portion and adapted to be electrically coupled to a first pole of the power supply;
    a connector fixedly engaged to the shaft proximal end portion adapted to couple the device to the power supply; and
    at least one temperature-indicating element disposed on an exterior of at least one of the electrode assembly and the shaft to be responsive to temperature changes adjacent to the device, wherein the temperature-indicating element undergoes a change in chromatic appearance over a pre-determined temperature range and wherein said at least one temperature-indicating element is a discrete section disposed axially proximal to said at least one active electrode.

2. The device of claim 1, wherein the pre-determined temperature range is about 40° C. to 95° C.

3. The device of claim 1, wherein the at least one temperature-indicating element is adapted to display a temperature value over the pre-determined temperature range.

4. The device of claim 1, wherein the at least one temperature-indicating element displays a message when exposed to a pre-defined temperature.

5. The device of claim 1, wherein the message is alphanumeric.

6. The device of claim 1, wherein the at least one temperature-indicating element comprises a thermochromic material.

7. The device of claim 1, wherein the at least one temperature-indicating element is adapted to substantially change from a first chromatic appearance to a second chromatic appearance when subject to the pre-determined temperature range and to substantially reverse from the second chromatic appearance to the first chromatic appearance when not subject to the pre-determined temperature range.

8. The device of claim 1, wherein the at least one temperature-indicating element comprises a thermochromic composition selected from the group consisting of a leuco dye and a liquid crystal.

9. The device of claim 1, wherein the at least one temperature-indicating element comprises a thermochromic paint or a thermochromic ink.

10. The device of claim 1, wherein the electrode assembly comprises a support matrix which contains at least one of the active electrodes, wherein the at least one temperature-indicating element is disposed on, or proximal to, the support matrix.

11. The device of claim 10, wherein at least one active electrode extends laterally from the shaft.

12. The device of claim 11, wherein the at least one temperature-indicating element is disposed on a portion of the shaft opposite the direction in which the active electrode extends.

13. The device of claim 1, wherein at least one active electrode extends distally from a distal tip of the shaft, and wherein the at least one temperature-indicating element is disposed proximal to the active electrode.

14. The device of claim 1, wherein the electrode assembly further comprises at least one return electrode adapted to be coupled to a second pole of the power supply and disposed at the distal end portion of the shaft, and wherein the at least one temperature-indicating element is disposed proximal, adjacent, or distal to the return electrode.

15. The device of claim 1, wherein the at least one temperature-indicating element has a length in the range of from about 1 mm to 3 cm, and a width in the range of from about 1 mm to 5 cm.

16. The device of claim 1, further comprising a fluid delivery element for providing an electrically conductive fluid capable of forming a conductive fluid path between the electrode assembly and return electrode.

17. The device of claim 1, wherein the at least one temperature-indicating element comprises an annular band having a thermochromic material incorporated therein.

18. The device of claim 1, wherein the shaft is at least partially encased within a sheath, the sheath encasing the at least one temperature-indicating element, and wherein the sheath comprises a biocompatible material.

19. The device of claim 1, wherein the at least one temperature-indicating element is thermally insulated or thermally isolated from a surface of the shaft.

20. The device of claim 1, wherein the at least one temperature-indicating element comprises a printable medium and a thermochromic pigment.

21. The device of claim 1, wherein the device comprises a bipolar electrosurgical device adapted for applying RF electrical energy to a target tissue.

22. The device of claim 1, wherein the at least one temperature-indicating element comprises a first color and changes appearance to a second color.

23. The device of claim 1, wherein the at least one temperature-indicating element is a first temperature indicating element and the pre-determined range is a first predetermined range, where the device further comprises a second temperature indicating element disposed on an exterior of the shaft, wherein the second temperature indicating element changes appearance over a second pre-determined temperature range.

24. The device of claim 23, wherein the first and second pre-determined ranges are substantially the same.

25. The device of claim 23, wherein the first and second pre-determined ranges are different.

26. The device of claim 1 wherein the at least one temperature-indicating element is located adjacent the electrode assembly.

27. The device of claim 26 wherein the at least one temperature-indicating element is located superior to the at least one active electrode.

28. The device of claim 1 wherein the at least one temperature-indicating element is located proximal to the electrode assembly.

29. The device of claim 1, wherein the connector comprises a cable having a distal end fixedly attached to the shaft proximal end portion, and a proximal portion adapted to engage the power supply.

30. The device of claim 1, wherein the connector is adapted to removably engage a cable where the cable couples the device to the power supply.

31. The device of claim 1, wherein at least one of the temperature-indicating elements is configured about the shaft so that at least a portion of the temperature-indicating element is viewable from any side of the shaft.

32. The device of claim 31, wherein the at least one of the temperature-indicating elements is placed circumferentially about the device shaft.

33. The device of claim 1, wherein the shaft is malleable.

34. A medical device for use with an energy delivery unit, comprising:
  a shaft having a shaft distal end portion and a shaft proximal end portion;
  an energy delivery assembly comprising at least one energy delivery element disposed near the shaft distal end portion, and an energy delivery return element disposed on said shaft distal end portion and spaced from said energy delivery element and adapted to be coupled to the energy delivery unit, said energy delivery element adapted to generate a tissue ablating plasma when a voltage difference is applied to said energy delivery element in the presence of an electrically conductive fluid;
  a connector fixedly engaged to the shaft proximal end portion and adapted to couple the device to the energy delivery unit; and
  a first means for providing a visual indication of a particular temperature or range of temperatures in a region adjacent a portion of the shaft and wherein at least a portion of said first means is disposed between said at least one energy delivery element and said return clement.

35. The device of claim 34, further comprising a second means for identifying a particular temperature or range of temperature in a region adjacent a portion of the shaft.

36. The device of claim 35, wherein said electrode assembly further comprises at least one return electrode adapted to be coupled to a second pole of the power supply.

37. The device of claim 35, wherein said first means for identifying is located adjacent the electrode assembly.

38. The device of claim 35, wherein said second means for identifying is located adjacent said first means for identifying.

39. The device of claim 35, wherein said second means for identifying is located along the shaft proximally to said first means for identifying.

40. The device of claim 34, wherein the connector comprises a cable having a distal end fixedly attached to the shaft proximal end portion, and a proximal portion adapted to engage the power supply.

41. The device of claim 34, wherein the connector is adapted to removably engage a cable where the cable couples the device to the power supply.

42. The device of claim 34, wherein the energy delivery assembly is adapted to provide energy selected from the group consisting of ultrasound, radio frequency energy, mechanical, laser, thermal, microwave, chemical, and radiation.

* * * * *